US008626284B2

(12) United States Patent  (10) Patent No.: US 8,626,284 B2
Onodera et al.  (45) Date of Patent: Jan. 7, 2014

(54) INTRACARDIAC DEFIBRILLATION CATHETER SYSTEM

(75) Inventors: Yutaka Onodera, Tokyo (JP); Yasuhiro Kojima, Tokyo (JP); Kenji Mori, Tokyo (JP); Yasuo Sakano, Tokyo (JP)

(73) Assignee: Japan Lifeline Co., Ltd., Tokyo (JP)

( * ) Notice: Subject to any disclaimer, the term of this patent is extended or adjusted under 35 U.S.C. 154(b) by 29 days.

(21) Appl. No.: 13/255,300

(22) PCT Filed: Feb. 23, 2010

(86) PCT No.: PCT/JP2010/052666
§ 371 (c)(1),
(2), (4) Date: Sep. 8, 2011

(87) PCT Pub. No.: WO2010/109997
PCT Pub. Date: Sep. 30, 2010

(65) Prior Publication Data
US 2011/0319948 A1  Dec. 29, 2011

(30) Foreign Application Priority Data
Mar. 23, 2009 (JP) ................................. 2009-070940

(51) Int. Cl.
*A61N 1/39* (2006.01)
*A61B 5/0428* (2006.01)
(52) U.S. Cl.
USPC ............................................. 607/5; 600/522
(58) Field of Classification Search
USPC .................... 607/5; 600/510, 522; 606/34, 42
See application file for complete search history.

(56) References Cited

U.S. PATENT DOCUMENTS

| 5,383,908 | A | | 1/1995 | Sweeney et al. |
| 5,405,375 | A | * | 4/1995 | Ayers et al. ................... 607/122 |
| 5,738,105 | A | | 4/1998 | Kroll |
| 5,855,592 | A | * | 1/1999 | McGee et al. .................... 607/4 |

(Continued)

FOREIGN PATENT DOCUMENTS

| CN | 1147964 A | 4/1997 |
| CN | 2375328 Y | 4/2000 |

(Continued)

OTHER PUBLICATIONS

Supplementary European Search Report mailed on Aug. 16, 2012 for EP 10 75 5798.

(Continued)

*Primary Examiner* — George Evanisko
(74) *Attorney, Agent, or Firm* — Holtz Holtz Goodman & Chick, PC

(57) ABSTRACT

An intracardiac defibrillation catheter system equipped with a defibrillation catheter, a power source device and an electrocardiograph. The defibrillation catheter is equipped with a first DC electrode group and a second DC electrode group. The power source device is equipped with a DC power source unit, a catheter-connected connector, an electrocardiograph-connected connector, an arithmetic processing unit, which controls the DC power source unit and has an output circuit for outputting a direct current voltage from the DC power source unit, and a changeover unit, in which the catheter-connected connector is connected to a common contact. The electrocardiograph-connected connector is connected to a first contact, and the arithmetic processing unit is connected to a second contact. In the intracardiac defibrillation catheter system, electric energy necessary and sufficient for defibrillation can be surely supplied. The defibrillation catheter can be used as an electrode catheter for cardiac potential measurement when a defibrillation treatment is not performed.

7 Claims, 17 Drawing Sheets

(56) References Cited

U.S. PATENT DOCUMENTS

| | | | |
|---|---|---|---|
| 6,178,355 | B1 | 1/2001 | Williams et al. |
| 6,201,994 | B1 | 3/2001 | Warman et al. |
| 6,438,426 | B2 * | 8/2002 | Hofstad et al. ............... 607/125 |
| 6,916,306 | B1 | 7/2005 | Jenkins et al. |
| 7,130,700 | B2 | 10/2006 | Gardeski et al. |
| 2003/0036774 | A1 * | 2/2003 | Maier et al. ...................... 607/5 |
| 2003/0125770 | A1 | 7/2003 | Fuimaono et al. |
| 2005/0113897 | A1 | 5/2005 | Seifert et al. |
| 2006/0184106 | A1 | 8/2006 | McDaniel et al. |
| 2011/0160785 | A1 | 6/2011 | Mori et al. |

FOREIGN PATENT DOCUMENTS

| | | | |
|---|---|---|---|
| CN | 101190146 | A | 6/2008 |
| JP | 2001-112874 | A | 4/2001 |
| JP | 2003-230635 | A | 8/2003 |
| JP | 2004-512894 | A | 4/2004 |
| JP | 2006-255401 | A | 9/2006 |
| JP | 2010-220778 | A | 7/2010 |
| WO | WO 00/32129 | A1 | 6/2000 |
| WO | WO 02/38052 | A2 | 5/2002 |
| WO | WO 02/38052 | A3 | 5/2002 |
| WO | WO 2005/002665 | A2 | 1/2005 |
| WO | WO 2006/068880 | A1 | 6/2006 |
| WO | WO 2007/130900 | A2 | 11/2007 |

OTHER PUBLICATIONS

Patent Examination Report No. 1 from the Australian Patent Office mailed on Sep. 20, 2012.
English-language International Preliminary Report on Patentability and Written Opinion of the International Searching Authority dated Oct. 18, 2011 for PCT/JP2010/052666 filed Feb. 23, 2010; Applicant: Japan Lifeline Co., Ltd.
Japanese Office Action mailed on May 21, 2010 for Japanese patent application 2009-070940.
Chinese Office Action issued on May 29, 2013 for Chinese patent application 201080007993.5.

* cited by examiner

A-A SECTION

INTRACARDIAC DEFIBRILLATION CATHETER SYSTEM

CROSS-REFERENCE TO RELATED APPLICATION

This application is a United States national phase application of International Application PCT/JP2010/052666 filed Feb. 23, 2010.

TECHNICAL FIELD

The present invention relates to an intracardiac defibrillation catheter system, and more particularly to a catheter system equipped with a defibrillation catheter inserted into a cardiac cavity, a power source device for applying a direct current (DC) voltage to electrodes of this defibrillation catheter, and an electrocardiograph.

BACKGROUND ART

An automated external defibrillator (AED) is known as a defibrillator for removing atrial fibrillation (see, for example, Patent Literature 1).

In a defibrillation treatment by the AED, an electrode pad is attached to the body surface of a patient to apply a DC voltage thereto, thereby giving electric energy within the body of the patient. Here, the electric energy flowing within the body of the patient from the electrode pad is generally controlled to 150 to 200 J, and a part (generally, about several % to 20%) thereof flows into a heart to be used for defibrillation treatment.

CITATION LIST

Patent Literature

Patent Literature 1: Japanese Patent Application Laid-Open No. 2001-112874

SUMMARY OF INVENTION

Technical Problem

And now, the atrial fibrillation is liable to occur during cardiac catheterization, and it is necessary to conduct electrical defibrillation even in this case.

According to the AED that electric energy is supplied from the outside of the body, however, it is difficult to supply effective electric energy (for example, 10 to 30 J) to a heart that has suffered the atrial fibrillation.

In other words, when a proportion of electric energy flowing into the heart of the electric energy supplied from the outside of the body is small (for example, about several %), it is impossible to conduct a sufficient defibrillation treatment.

On the other hand, when the electric energy supplied from the outside of the body flows into the heart in a high proportion, it is considered that the tissue of the heart may possibly be damaged.

In addition, in the defibrillation treatment by the AED, burn is easy to occur on the body surface to which the electrode pad has been attached. When the proportion of the electric energy flowing into the heart is small as described above, the degree of burn becomes heavy by supplying the electric energy repeatedly to be a considerable burden on the patient subjected to the catheterization.

The present invention has been made on the basis of the foregoing circumstances and has as an object the provision of an intracardiac defibrillation catheter system capable of surely supplying electric energy necessary and sufficient for defibrillation to a heart that has suffered atrial fibrillation during cardiac catheterization.

Another object of the present invention is to provide an intracardiac defibrillation catheter system by which a defibrillation treatment can be conducted without causing burn on the body surface of a patient.

A further object of the present invention is to provide an intracardiac defibrillation catheter system, the defibrillation catheter of which can be used as an electrode catheter for cardiac potential measurement when no defibrillation treatment is performed.

Solution to Problem (1) The intracardiac defibrillation catheter system according to the present invention is a catheter system comprising a defibrillation catheter inserted into a cardiac cavity to conduct defibrillation, a power source device for applying a direct current voltage to electrodes of this defibrillation catheter, and an electrocardiograph, wherein the defibrillation catheter comprises an insulated tube member, a first electrode group (a first DC electrode group) composed of a plurality of ring-like electrodes and installed in a distal region of the tube member, a second electrode group (a second DC electrode group) composed of a plurality of ring-like electrodes and installed on the tube member towards proximal direction (with a space on a proximal side) from the first DC electrode group, a first lead wire group composed of a plurality of lead wires whose distal ends are connected to the respective electrodes making up the first DC electrode group, and a second lead wire group composed of a plurality of lead wires whose distal ends are connected to the respective electrodes making up the second DC electrode group, wherein the power source device comprises a DC power source unit, a catheter-connected connector connected to proximal sides of the first lead wire group and the second lead wire group of the intracardiac defibrillation catheter, an electrocardiograph-connected connector connected to an input terminal of the electrocardiograph, an arithmetic processing unit which controls the DC power source unit based on input of an external switch and has an output circuit for outputting a direct current voltage from the DC power source unit, and a changeover unit composed of a changeover switch of two contacts per circuit, in which the catheter-connected connector is connected to a common contact, the electrocardiograph-connected connector is connected to a first contact, and the arithmetic processing unit is connected to a second contact, wherein when a cardiac potential is measured by the electrodes (electrodes making up the first DC electrode group and/or the second DC electrode group) of the defibrillation catheter, the first contact in the changeover unit is selected, and cardiac potential information from the defibrillation catheter is inputted into the electrocardiograph via the catheter-connected connector, the changeover unit and the electrocardiograph-connected connector of the power source device, and wherein when defibrillation is conducted by the defibrillation catheter, the contact of the changeover unit is changed over to the second contact by the arithmetic processing unit of the power source device to respectively apply voltages different in polarity from each other to the first DC electrode group and the second DC electrode group of the defibrillation catheter via the output circuit of the arithmetic processing unit, the changeover unit and the catheter-connected connector from the DC power source unit.

The defibrillation catheter making up the intracardiac defibrillation catheter system according to the present invention is inserted into a cardiac cavity in such a manner that the first DC electrode group is located in a coronary vein, and the second DC electrode group is located in a right atrium to respectively apply voltages different in polarity from each other to the first DC electrode group and the second DC electrode group (apply a direct current voltage between the first DC electrode group and the second DC electrode group) through the first lead wire group and the second lead wire group by the power source device, thereby directly applying electric energy to a heart that has suffered fibrillation to conduct a defibrillation treatment.

As described above, the electric energy is directly given to the heart that has suffered the fibrillation by the first DC electrode group and the second DC electrode group of the defibrillation catheter arranged within the cardiac cavity, whereby electric stimulus (electric shock) necessary and sufficient for defibrillation treatment can be surely given only to the heart.

In addition, no burn is caused on the body surface of the patient because the electric energy can be directly applied to the heart.

The first contact is selected in the changeover unit making up the power source device, whereby a route from the catheter-connected connector to the electrocardiograph-connected connector is ensured, so that a cardiac potential can be measured by the electrodes making up the first DC electrode group and/or the second DC electrode group of the defibrillation catheter, and the resultant cardiac potential information can be inputted into the electrocardiograph via the catheter-connected connector, the changeover unit and the electrocardiograph-connected connector.

In other words, when a defibrillation treatment is not necessary during cardiac catheterization, the defibrillation catheter making up the present invention can be used as an electrode catheter for cardiac potential measurement. As a result, such troubles as to remove an electrode catheter to newly insert a catheter for defibrillation when atrial fibrillation has occurred during cardiac catheterization can be saved.

(2) It may be preferable that the defibrillation catheter making up the intracardiac defibrillation catheter system according to the present invention comprises a potential-measuring electrode group composed of a plurality of electrodes installed on the tube member apart from the first DC electrode group or the second DC electrode group, and a lead wire group for potential measurement, which is composed of a plurality of lead wires whose distal ends are connected to the respective electrodes making up the potential-measuring electrode group, and whose proximal ends are connected to the catheter-connected connector of the power source device, a route linking the catheter-connected connector to the electrocardiograph-connected connector is formed in the power source device, and the cardiac potential information measured by the electrodes making up the potential-measuring electrode group is inputted into the electrocardiograph via the electrocardiograph-connected connector from the catheter-connected connector of the power source device without going through the changeover unit.

According to such a structure, the electrocardiograph can acquired the cardiac potential measured by the potential-measuring electrode group even upon defibrillation treatment during which the electrocardiograph cannot acquire the cardiac potential from the first DC electrode group and the second DC electrode group of the defibrillation catheter, so that the defibrillation treatment can be conducted while monitoring the cardiac potential in the electrocardiograph.

(3) Another cardiac potential-measuring means than the defibrillation catheter may preferably be connected to the electrocardiograph making up the intracardiac defibrillation catheter system according to the present invention.

(4) In addition, this cardiac potential-measuring means may preferably be an electrode pad or an electrode catheter.

According to such a structure, the electrocardiograph can acquired the cardiac potential measured by the cardiac potential-measuring means even upon defibrillation treatment during which the electrocardiograph cannot acquire the cardiac potential from the first DC electrode group and the second DC electrode group of the defibrillation catheter, so that the defibrillation treatment can be conducted while monitoring the cardiac potential in the electrocardiograph.

(5) It may be preferable that the power source device making up the intracardiac defibrillation catheter system according to the present invention comprises an electrocardiogram input connector connected to the arithmetic processing unit and an output terminal of the electrocardiograph, and a display means connected to the arithmetic processing unit, and the cardiac potential information inputted into the electrocardiogram input connector from the electrocardiograph is inputted into the arithmetic processing unit and displayed on the display means.

According to such a structure, a part of the cardiac potential information (the cardiac potential acquired by the electrodes making up the first DC electrode group and/or the second DC electrode group of the defibrillation catheter, the cardiac potential acquired by the electrodes making up the potential-measuring electrode group of the defibrillation catheter, or the cardiac potential acquired by said another cardiac potential-measuring means than the defibrillation catheter) is inputted into the arithmetic processing unit, and the DC power source unit can be controlled on the basis of this cardiac potential information in the arithmetic processing unit.

In addition, the defibrillation treatment (for example, input of the external switch) can be conducted while monitoring the cardiac potential information (waveform) inputted into the arithmetic processing unit by the display means.

(6) The arithmetic processing unit of the power source device making up the intracardiac defibrillation catheter system according to the present invention may preferably conduct arithmetic, processing so as to apply a voltage synchronizing with the cardiac potential waveform inputted via the electrocardiogram input connector to control the DC power source unit.

According to such a structure, the voltage can be applied synchronizing with the cardiac potential waveform to effectively conduct the defibrillation treatment.

(7) The arithmetic processing unit of the power source device making up the intracardiac defibrillation catheter system according to the present invention may preferably measure a resistance between the first DC electrode group and the second DC electrode group prior to the application of the voltage to judge whether the resistance measured exceeds a fixed value or not, and send the DC power source unit a control, signal to the effect that the voltage is applied only when the resistance does not exceed the fixed value.

According to such a structure, the voltage can be applied only when the first DC electrode group and the second DC electrode group of the defibrillation catheter have been brought into sure contact with respective predetermined sites (for example, a vessel wall of the coronary vein and an inner wall of the right atrium), so that the defibrillation treatment can be effectively conducted.

Advantageous Effects of Invention

According to the intracardiac defibrillation catheter system of the present invention, electric energy necessary and sufficient for defibrillation can be surely supplied to a heart that has suffered atrial fibrillation during cardiac catheterization. In addition, no burn is caused on the body surface of a patient, and invasiveness is also little.

Further, the defibrillation catheter making up the present invention can be used as an electrode catheter for cardiac potential measurement when the defibrillation treatment is not necessary.

DESCRIPTION OF EMBODIMENTS

<First Embodiment>

Figure 1:
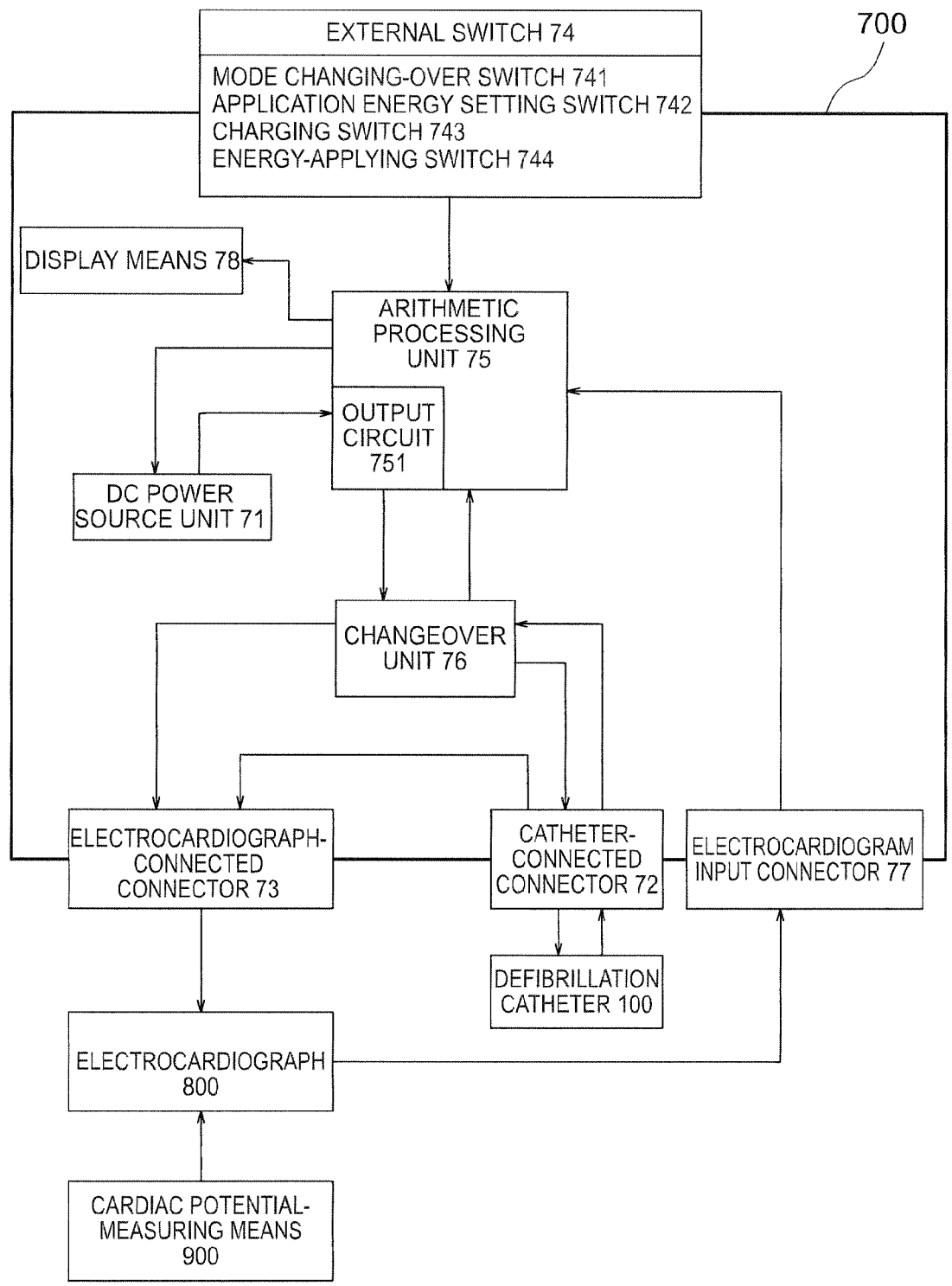
[FIG. 1] is a block diagram illustrating an embodiment of an intracardiac defibrillation catheter system according to the present invention.
Figure 2:
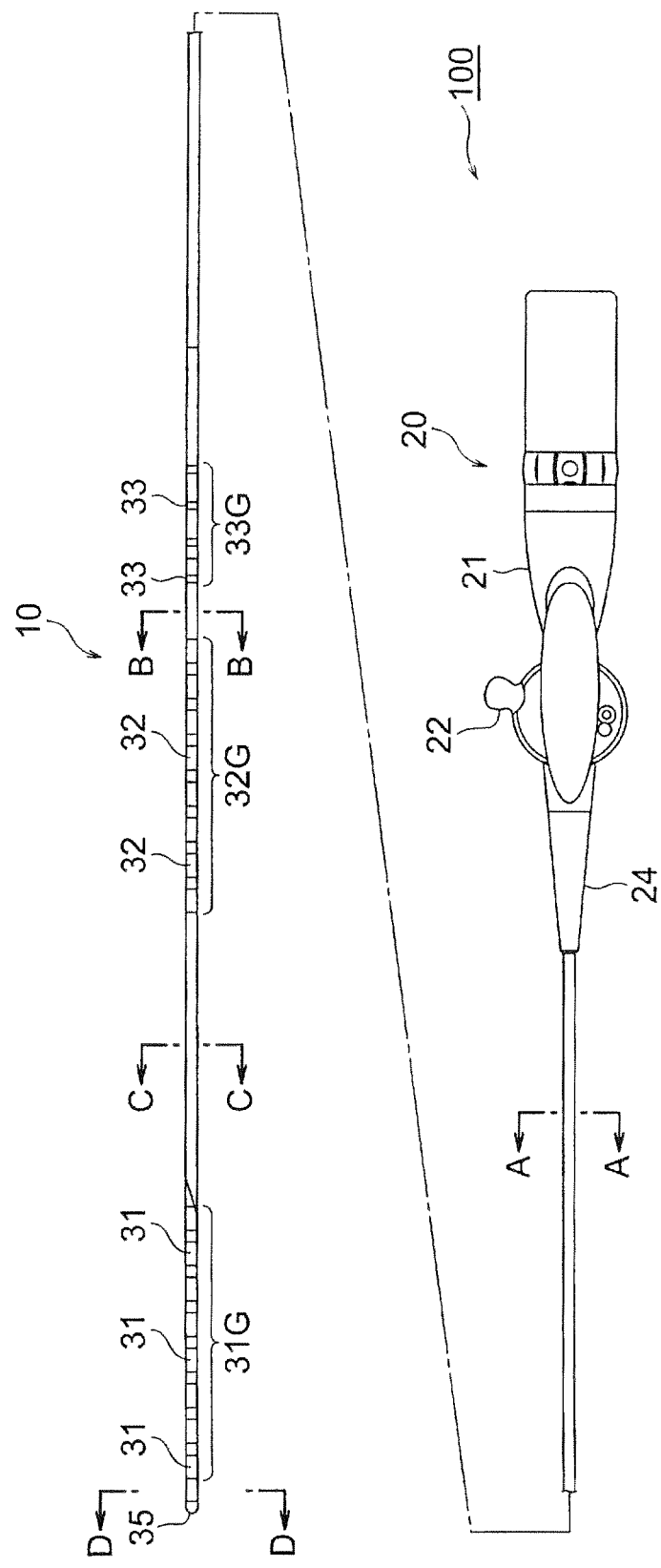
[FIG. 2] is an explanatory plan view illustrating a defibrillation catheter making up the catheter system illustrated in FIG. 1.

As illustrated in FIG. 1, the intracardiac defibrillation catheter system according to this embodiment is equipped with a defibrillation catheter 100, a power source device 700, an electrocardiograph 800 and a cardiac potential-measuring means 900.

As illustrated in FIGS. 2 to 5, the defibrillation catheter 100 making up the catheter system according to this embodiment is equipped with a multi-lumen tube 10, a handle 20, a first DC electrode group 31G, a second DC electrode group 32G, a proximal-side potential-measuring electrode group 33G, a first lead wire group 41G, a second lead wire group 42G and a third lead wire group 43G.

Figure 4:
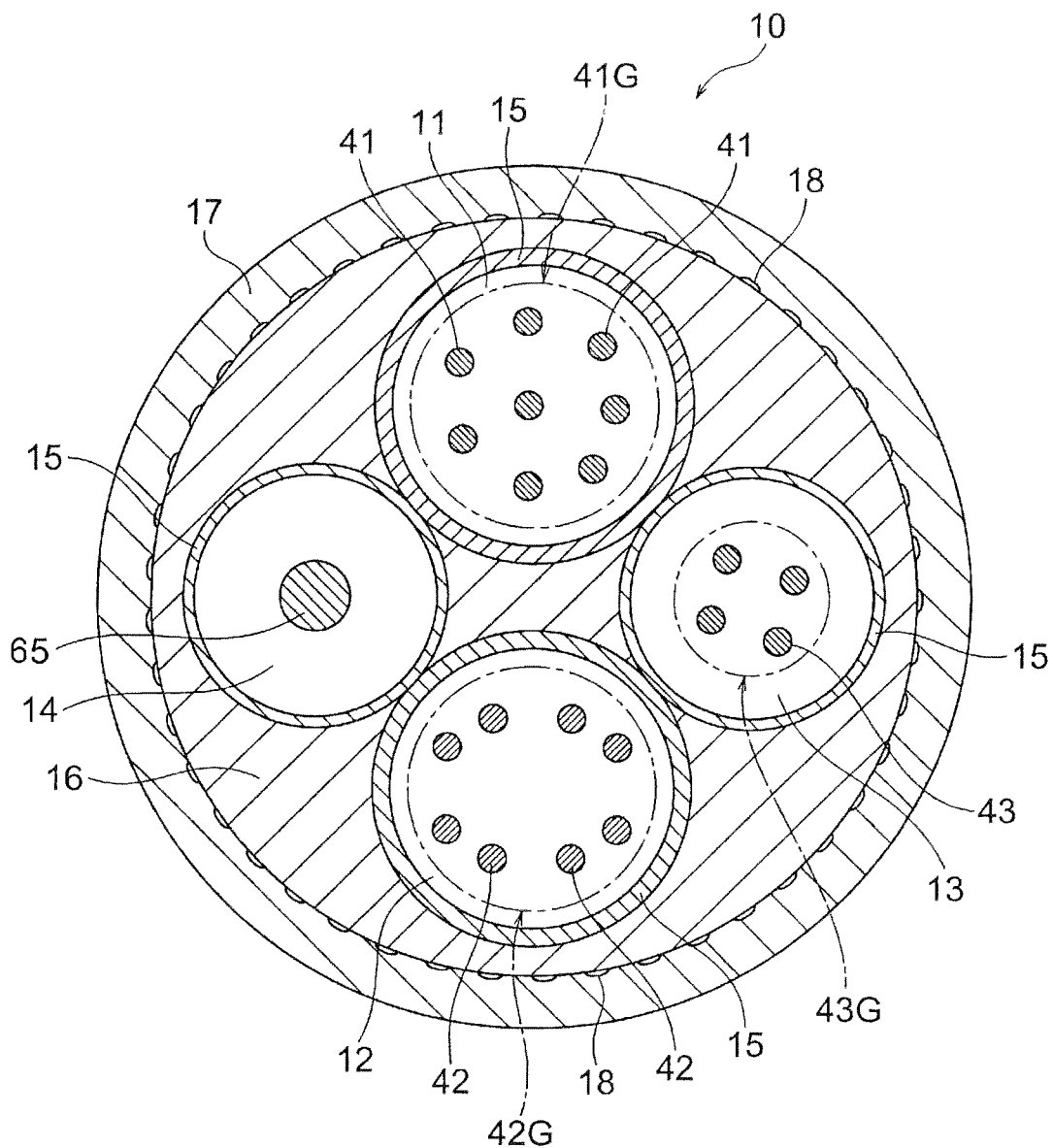
[FIG. 4] is a cross-sectional view illustrating a section A-A in FIG. 2.
Figure 5:
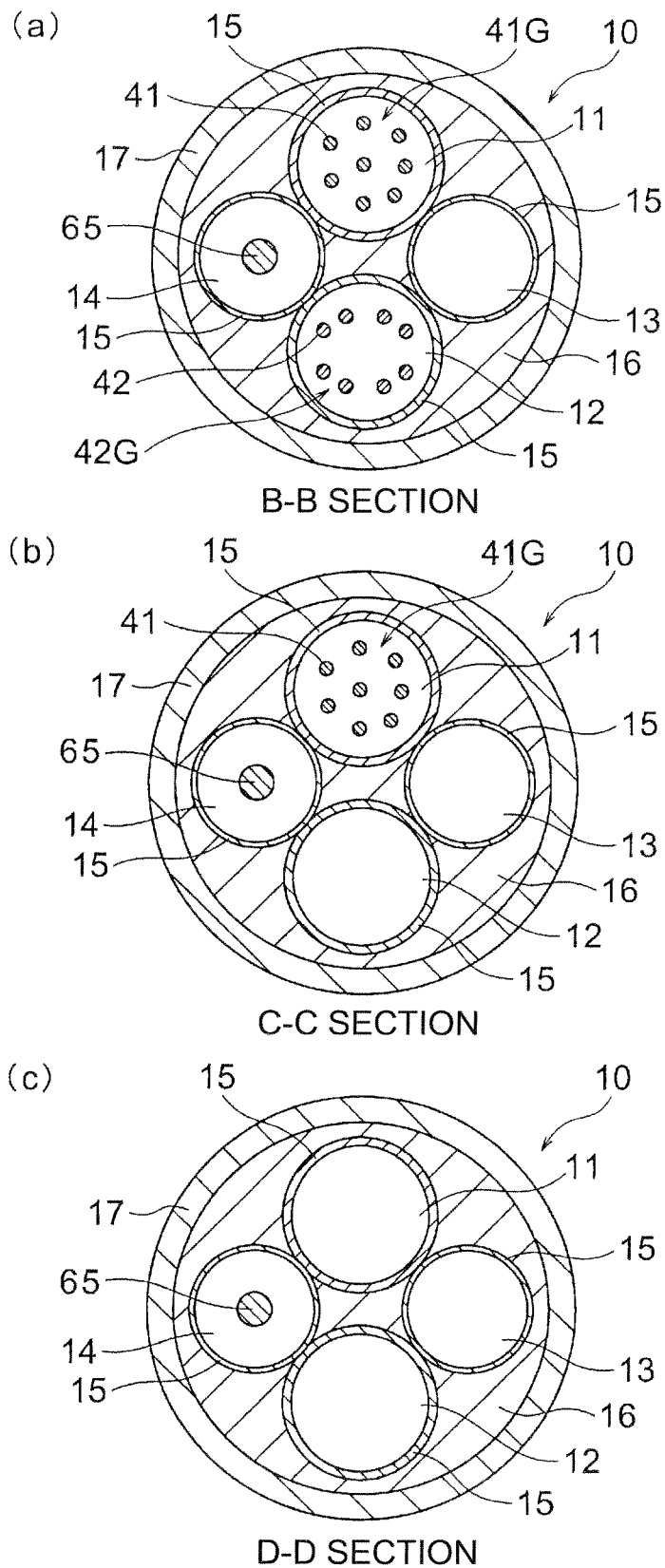
[FIG. 5] is cross-sectional views illustrating sections B-B, C-C and D-D in FIG. 2.

As illustrated in FIGS. 4 and 5, four lumens (a first lumen 11, a second lumen 12, a third lumen 13 and a fourth lumen 14) are formed in the multi-lumen tube (an insulated tube member having a multi-lumen structure) making up the defibrillation catheter 100.

In FIGS. 4 and 5, reference signs 15, 16 and 17 designate a fluororesin layer partitioning into the lumens, an inner (core) part composed of a nylon elastomer having a low hardness and an outer (shell) part composed of a nylon elastomer having a high hardness, respectively. In FIG. 4, reference sign 18 designates a stainless steel wire forming a braid.

The fluororesin layer 15 partitioning into the lumens is formed of a material having high insulating property, for example, a perfluoroalkyl vinyl ether copolymer (PFA) or polytetrafluoroethylene (PTFE).

The nylon elastomer forming the outer part 17 of the multi-lumen tube 10, having different hardnesses in an axial direction, is used, whereby the multi-lumen tube 10 is formed in such a manner that the hardness becomes higher stepwise toward the proximal side from the distal side.

Figure 3:
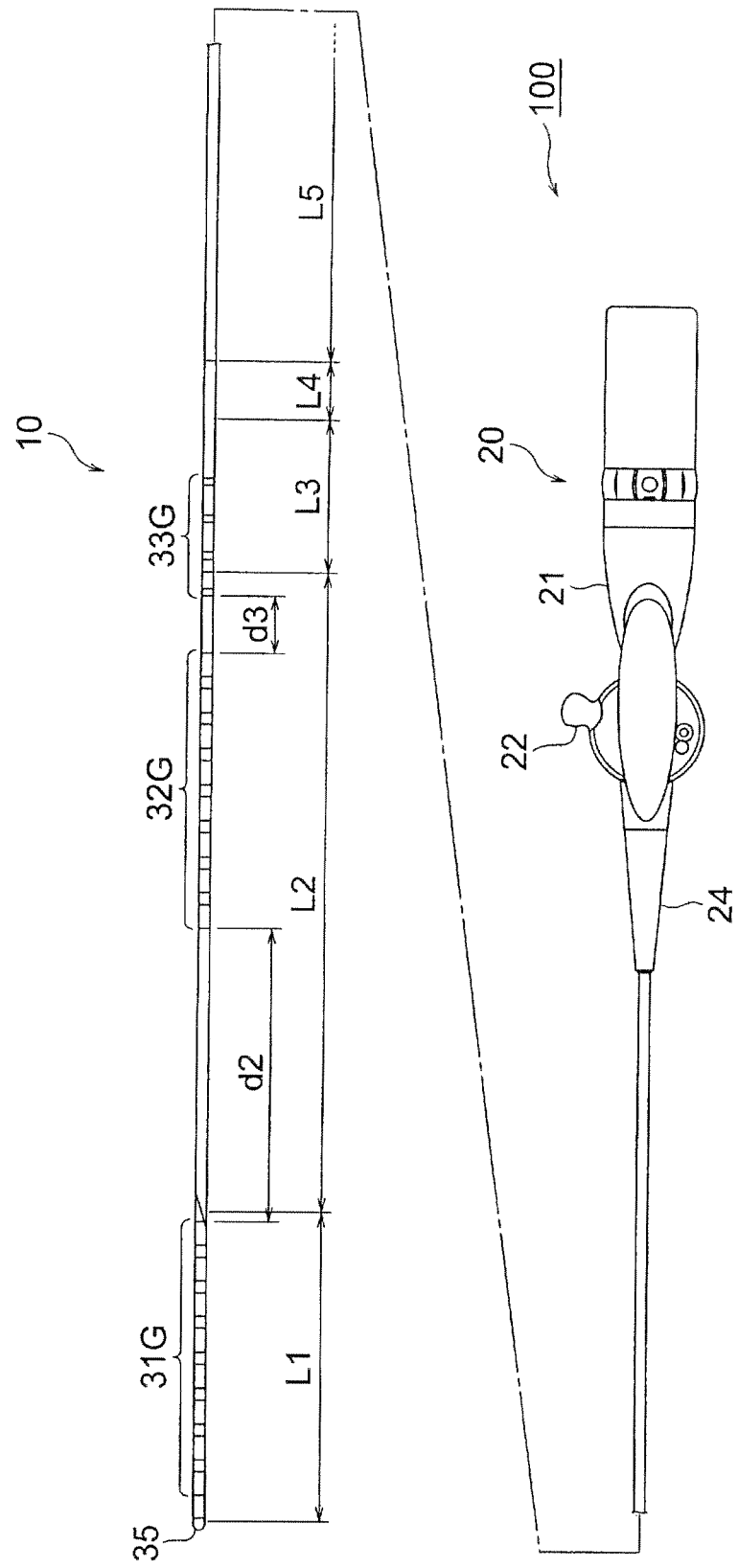
[FIG. 3] is an explanatory plan view (drawing for explaining dimensions and hardnesses) illustrating the defibrillation catheter making up the catheter system illustrated in FIG. 1.

As a preferable example, the hardness (hardness as measured by a D-type hardness meter) in a region indicated by L1 (length: 52 mm) in FIG. 3 is 40, the hardness in a region indicated by L2 (length: 108 mm) is 55, the hardness in a region indicated by L3 (length: 25.7 mm) is 63, the hardness in a region indicated by L4 (length: 10 mm) is 68, and the hardness in a region indicated by L5 (length: 500 mm) is 72.

The braid formed by the stainless steel wire 18 is formed in only the region indicated by L5 in FIG. 3 and is provided between the inner part 16 and the outer part 17 as illustrated in FIG. 4.

The outer diameter of the multi-lumen tube 10 is, for example, 1.2 to 3.3 mm.

No particular limitation is imposed on a method for producing the multi-lumen tube 10.

The handle 20 making up the defibrillation catheter 100 according to this embodiment is equipped with a handle body 21, a lug 22 and a strain relief 24.

The lug 22 is rotationally operated, whereby a distal end portion of the multi-lumen tube 10 can be deflected (oscillated).

The first DC electrode group 31G, the second DC electrode group 32G and the proximal-side potential-measuring electrode group 33G are installed on an outer periphery (a distal region where no braid is formed in the interior thereof) of the multi-lumen tube 10. Here, "the electrode group" means an assembly of a plurality of electrodes that are installed at narrow intervals (for example, 5 mm or less), and form the same pole (have the same polarity) or have the same object.

The first DC electrode group is composed of a plurality of electrodes forming the same pole (minus pole or plus pole) and installed at narrow intervals in the distal region of the multi-lumen tube. Here, the number of the electrodes making up the first DC electrode group is, for example, 4 to 13, preferably 8 to 10 though it varies according to the width of individual electrodes and arrangement interval.

In this embodiment, the first DC electrode group 31G is made up of 8 ring-like electrodes 31 installed in the distal region of the multi-lumen tube 10.

The electrodes 31 making up the first DC electrode group 31G are connected to a catheter-connected connector of the power source device 700 through lead wires (lead wires 41 making up the first lead wire group 41G) and a connector which will be described subsequently.

Here, the width (length in an axial direction) of the electrode 31 is preferably 2 to 5 mm, and is 4 mm as a preferable example.

If the width of the electrode 31 is too narrow, the quantity of heat generated upon application of voltage becomes excessive, and so there is a possibility that a surrounding tissue may be damaged. If the width of the electrode 31 is too wide on the other hand, the flexibility or softness of a portion of the multi-lumen tube 10, in which the first DC electrode group 31G is provided, may be impaired in some cases.

An installation interval (clearance distance between adjoining electrodes) between the electrodes 31 is preferably 1 to 5 mm, and is 2 mm as a preferable example.

The first DC electrode group 31G is located in, for example, a coronary vein upon use (upon arrangement into a cardiac cavity) of the defibrillation catheter 100.

The second DC electrode group is composed of a plurality of electrodes forming a pole (plus pole or minus pole) opposite to the first DC electrode group and installed at narrow intervals on the multi-lumen tube towards proximal direction from the installation position of the first DC electrode group. Here, the number of the electrodes making up the second DC electrode group is, for example, 4 to 13, preferably 8 to 10 though it varies according to the width of individual electrodes and arrangement interval.

In this embodiment, the second DC electrode group 32G is made up of 8 ring-like electrodes 32 installed on the multi-lumen tube 10 towards proximal direction from the installation position of the first DC electrode group 31G.

The electrodes 32 making up the second DC electrode group 32G are connected to the catheter-connected connector of the power source device 700 through lead wires (lead wires 42 making up the second lead wire group 41G) and a connector which will be described subsequently.

Here, the width (length in an axial direction) of the electrode 32 is preferably 2 to 5 mm, and is 4 mm as a preferable example.

If the width of the electrode 32 is too narrow, the quantity of heat generated upon application of voltage becomes excessive, and so there is a possibility that a surrounding tissue may be damaged. If the width of the electrode 32 is too wide on the other hand, the flexibility or softness of a portion of the multi-lumen tube 10, in which the second DC electrode group 32G is provided, may be impaired in some cases.

An installation interval (clearance distance between adjoining electrodes) between the electrodes 32 is preferably 1 to 5 mm, and is 2 mm as a preferable example.

The second DC electrode group 32C is located in, for example, a right atrium upon use (upon arrangement into a cardiac cavity) of the defibrillation catheter 100.

In this embodiment, the proximal-side potential-measuring electrode group 33G is made up of 4 ring-like electrodes 33 installed on the multi-lumen tube 10 towards proximal direction from the installation position of the second DC electrode group 32G.

The electrodes 33 making up the proximal-side potential-measuring electrode group 33G are connected to the catheter-connected connector of the power source device 700 through lead wires (lead wires 43 making up the third lead wire group 43G) and a connector which will be described subsequently.

Here, the width (length in an axial direction) of the electrode 33 is preferably 0.5 to 2.0 mm, and is 1.2 mm as a preferable example.

If the width of the electrode 33 is too wide, the measurement accuracy of a cardiac potential is lowered, and it is difficult to ascertain a site where an abnormal potential has been generated.

An installation interval (clearance distance between adjoining electrodes) between the electrodes 33 is preferably 1.0 to 10.0 mm, and is 5 mm as a preferable example.

The proximal-side potential-measuring electrode group 33G is located in, for example, a superior vena cava where an abnormal potential tends to generate upon use (upon arrangement into a cardiac cavity) of the defibrillation catheter 100.

A distal-end tip 35 is installed on the distal end of the defibrillation catheter 10.

This distal-end tip 35 is neither connected to a lead wire nor used as an electrode in this embodiment. However, this tip may also be used as an electrode by connecting a lead wire thereto. As a material forming the distal-end tip 35, a metallic material such as platinum or stainless steel, or any one of various resin materials may be used without particular limitation.

A clearance distance d2 between the first DC electrode group 31G (proximal-side electrode 31) and the second DC electrode group 32G (distal-side electrode 32) is preferably 40 to 100 mm, and is 66 mm as a preferable example.

A clearance distance d3 between the second DC electrode group 32G (proximal-side electrode 32) and the proximal-side potential-measuring electrode group 33G (distal-side electrode 33) is preferably 5 to 50 mm, and is 30 mm as a preferable example.

The electrodes 31, 32 and 33 making up the first DC electrode group 31G, the second DC electrode group and the proximal-side potential-measuring electrode group 33G are preferably formed of platinum or a platinum-based alloy for the purpose of making contrasting characteristic for X-ray good.

The first lead wire group 41G illustrated in FIGS. 4 and 5 is an assembly of 8 lead wires 41 respectively connected to the 8 electrodes (31) making up the first DC electrode group (31G).

Each of the 8 electrodes 31 making up the first DC electrode group 31G can be electrically connected to the power source device 700 through the first lead wire group 41G (lead wire 41).

The 8 eletrodes 31 making up the first DC electrode group 31G are respectively connected to the separate lead wires 41.

Each of the lead wires 41 is welded at its distal end portion to an inner peripheral surface of the electrode 31 and enters the first lumen 11 from a side hole formed in a tube wall of the multi-lumen tube 10. The 8 lead wires 41 entered into the first lumen 11 extend into the first lumen 11 as the first lead wire group 41G.

The second lead wire group 42G illustrated in FIGS. 4 and 5 is an assembly of 8 lead wires 42 respectively connected to the 8 electrodes (32) making up the second DC electrode group (32G).

Each of the 8 electrodes 32 making up the second DC electrode group 32G can be electrically connected to the power source device 700 through the second lead wire group 42G (lead wire 42).

The 8 electrodes 32 making up the second DC electrode group 32G are respectively connected to the separate lead wires 42. Each of the lead wires 42 is welded at its distal end portion to an inner peripheral surface of the electrode 32 and enters the second lumen 12 (lumen different from the first lumen 11 to which the first lead wire group 41G extends) from a side hole formed in the tube wall of the multi-lumen tube 10. The 8 lead wires 42 entered into the second lumen 12 extend into the second lumen 12 as the second lead wire group 42G.

The first lead wire group 41G extends into the first lumen 11, and the second lead wire group 42G extends into the second lumen 12 as described above, whereby both lead wire groups are completely insulated and isolated from each other within the multi-lumen tube 10. Thus, short circuit between the first lead wire group 41G (first DC electrode group 31G) and the second lead wire group 42G (second DC electrode group 32G) can be surely prevented when the voltage necessary for the defibrillation is applied.

The third lead wire group 43S illustrated in FIG. 4 is an assembly of 4 lead wire 43 respectively connected to the electrodes (33) making up the proximal-side potential-measuring electrode group (33G).

Each of the electrodes 33 making up the proximal-side potential-measuring electrode group 33G can be connected to the power source device 700 through the third lead wire group 43G (lead wire 43).

The 4 electrodes 33 making up the proximal-side potential-measuring electrode group 33G are respectively connected to the separate lead wires 43. Each of the lead wires 43 is welded at its distal end portion to an inner peripheral surface of the electrode 33 and enters the third lumen 13 from a side hole formed in the tube wall of the multi-lumen tube 10. The 4 lead wires 43 entered into the third lumen 13 extend into the third lumen 13 as the third lead wire group 43G.

The third lead wire group 43G extending into the third lumen 13 as described above is completely insulated and isolated from both first lead wire group 41G and second lead wire group 42G. Thus, short circuit between the third lead wire group 43G (proximal-side potential-measuring electrode group 33G) and the first lead wire group 41G (first DC electrode group 31G) or the second lead wire group 42G (second DC electrode group 32G) can be surely prevented when the voltage necessary for the defibrillation is applied.

The lead wires 41, the lead wires 42 and the lead wire 43 are each composed of a resin-coated wire obtained by coating an outer periphery of a metal conductor with a resin such as polyimide. Here, the coating thickness of the resin is controlled to about 2 to 30 μm.

In FIGS. 4 and 5, reference sign 65 designates a pull wire. The pull wire 65 extends into the fourth lumen 14 and is located eccentrically from a central axis of the multi-lumen tube 10.

A distal end portion of the pull wire 65 is fixed to the distal-end tip 35 with solder. A large-diameter portion (retaining portion) for fall stopping may be formed at the tip of the pull wire 65. The distal-end tip 35 can be thereby firmly bonded to the pull wire 65 to surely prevent the distal-end tip 35 from falling.

On the other hand, a proximal end portion of the pull wire 65 is connected to the lug 22 of the handle 20, and the pull wire 65 is pulled by operating the lug 22, whereby a distal end portion of the multi-lumen tube 10 is deflected.

The pull wire 65 is formed by a stainless steel or Ni—Ti-based super-elastic alloy. However, the pull wire may not necessarily formed by a metal. The pull wire 65 may be formed by, for example, a nonconductive wire having high strength.

Incidentally, the mechanism for deflecting the distal end portion of the multi-lumen tube is not limited to this, and it may be constructed by providing, for example, a plate spring.

Only the pull wire 65 extends into the fourth lumen 14 of the multi-lumen tube 10, and no lead wire (group) extends. The lead wires can thereby be prevented from being damaged (for example, abraded) by the pull wire 65 moving in the axial direction upon the distal end deflection operation of the multi-lumen tube 10.

In the defibrillation catheter 100 according to this embodiment, the first lead wire group 41G, the second lead wire group 42G and the third lead wire group 43G are insulated and isolated from one another even in the interior of the handle 20.

Figure 6:
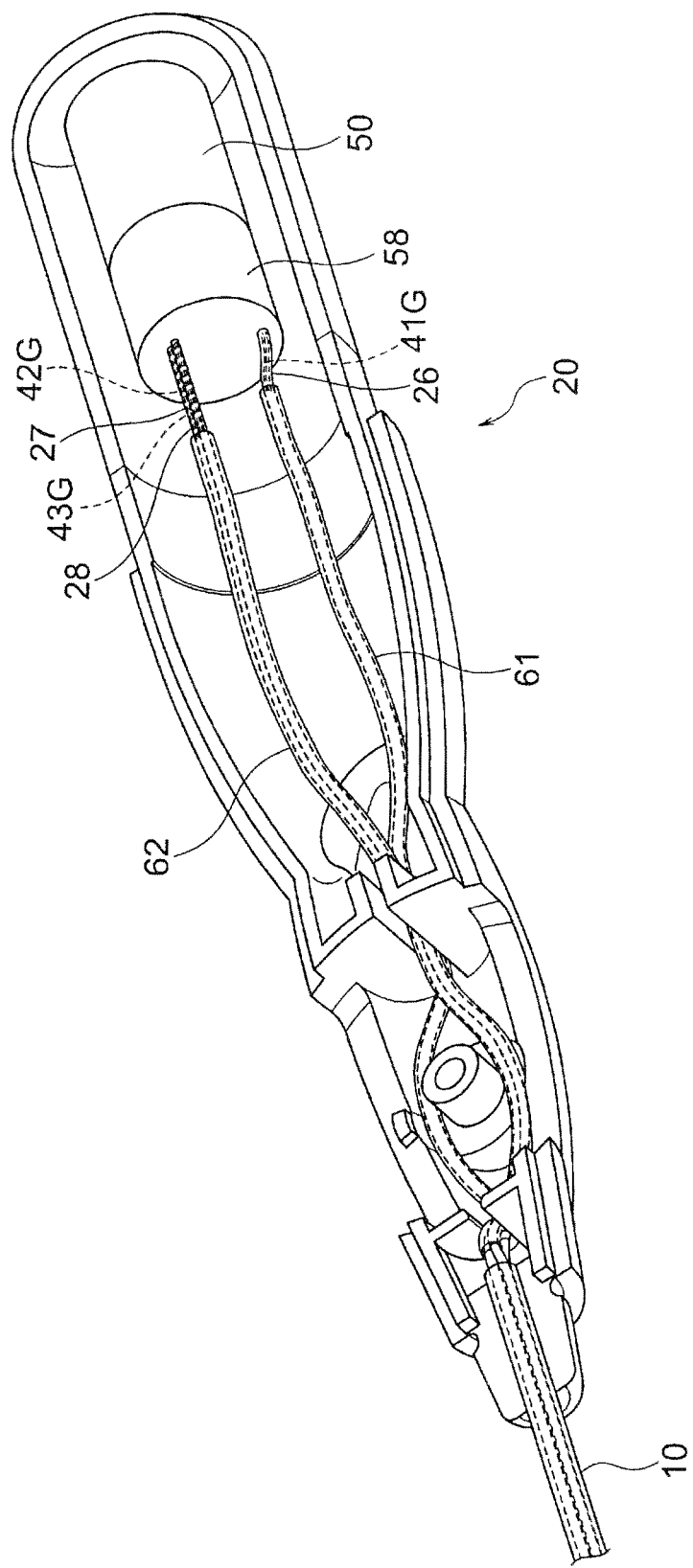
[FIG. 6] is a perspective view illustrating the interior structure of a handle according to an embodiment in the defibrillation catheter illustrated in FIG. 2.
Figure 7:
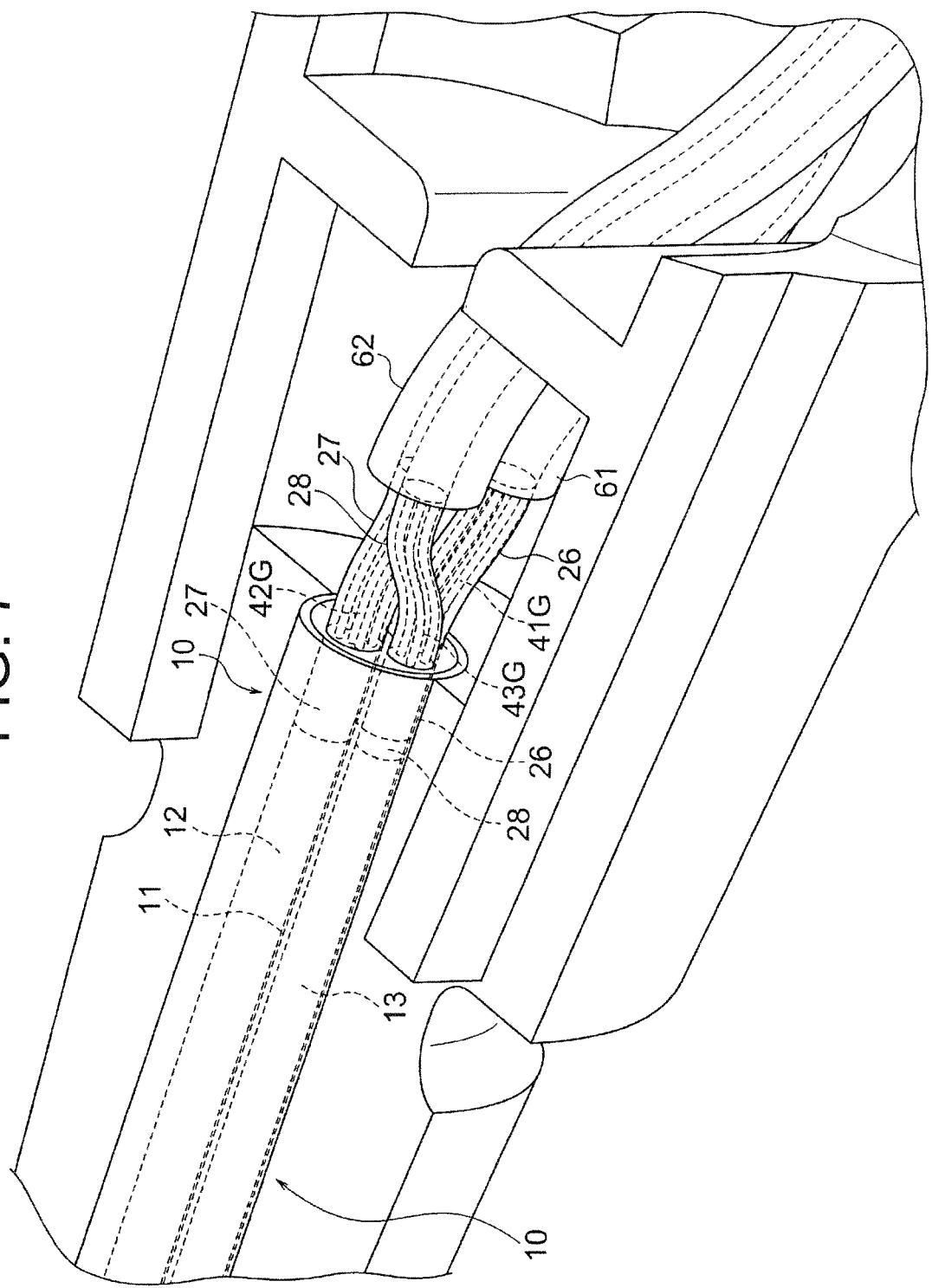
[FIG. 7] is a partly enlarged view of the interior (distal end side) of the handle illustrated in FIG. 6.
Figure 8:
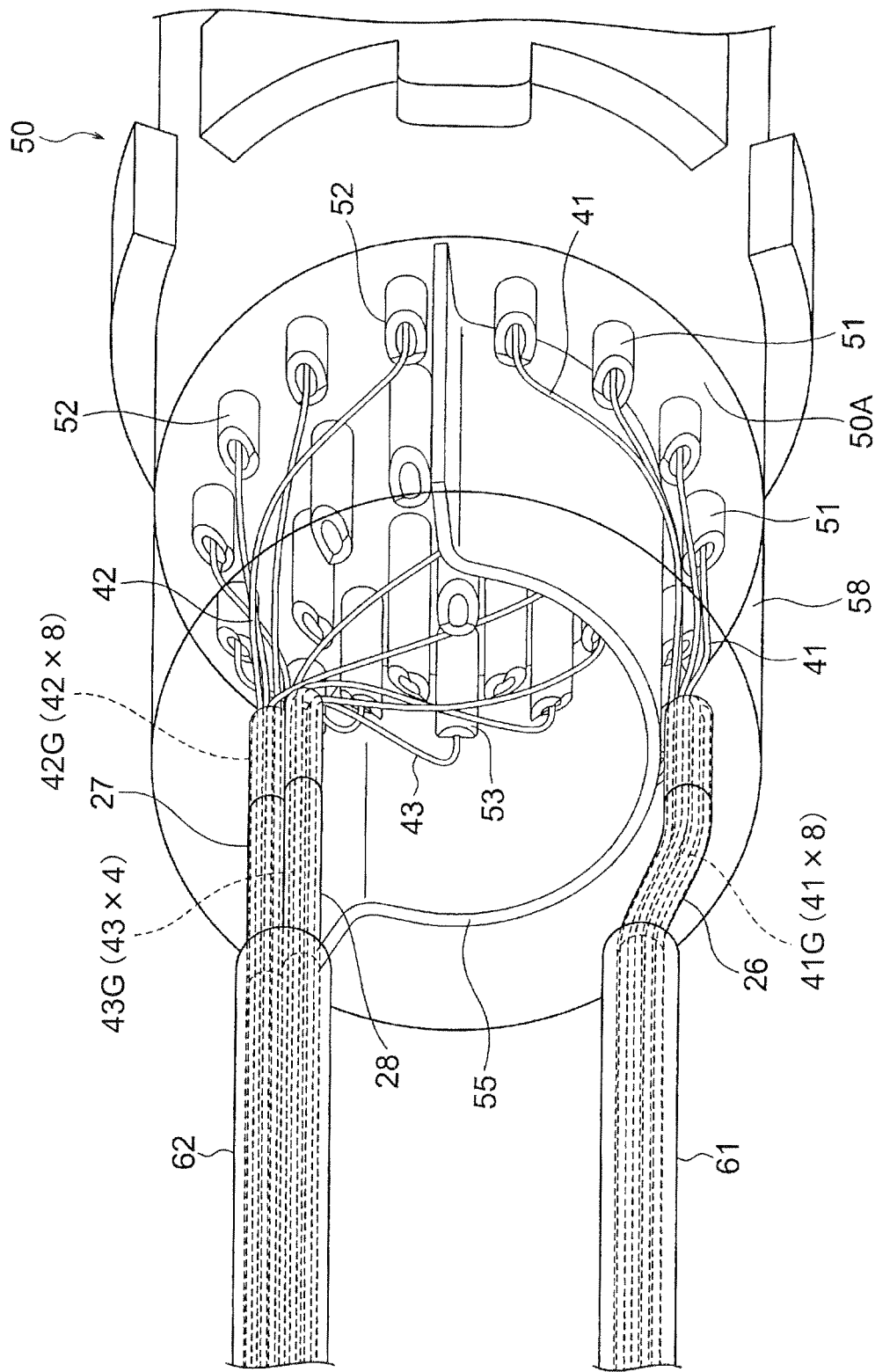
[FIG. 8] is a partly enlarged view of the interior (proximal end side) of the handle illustrated in FIG. 6.

FIG. 6 is a perspective view illustrating the interior structure of the handle of the defibrillation catheter 100 according to this embodiment, FIG. 7 is a partly enlarged view of the interior (distal end side) of the handle, and FIG. 8 is a partly enlarged view of the interior (proximal end side) of the handle.

As illustrated in FIG. 6, the proximal end portion of the multi-lumen tube 10 is inserted into a distal end opening of the handle 20, whereby the multi-lumen tube 10 is connected to the handle 20.

As illustrated in FIGS. 6 and 8, a cylindrical connector 50, in the distal end surface 50A of which a plurality of pin terminals (51, 52 and 53) projecting in a distal direction is arranged, is built in a proximal end portion of the handle 20.

As illustrated in FIGS. 6 to 8, 3 insulated tubes (first insulated tube 26, second insulated tube 27 and third insulated tube 28), into which the respective lead wire groups (first lead wire group 41G, second lead wire group 42G and third lead wire group 43G) are inserted, extend in the interior of the handle 20.

As illustrated in FIGS. 6 and 7, a distal end portion (portion about 10 mm long from the tip) of the first insulated tube 26 is inserted into the first lumen 11 of the multi-lumen tube 10, whereby the first insulated tube 26 is connected to the first lumen 11 into which the first lead wire group 41G extends.

The first insulated tube 26 connected to the first lumen 11 passes through an inner hole of a first protecting tube 61 extending in the interior of the handle 20 and extends up to the neighborhood of the connector 50 (distal end surface 50A in which the pin terminals have been arranged) to form a passage through which the proximal end portion of the first lead wire group 41G is guided to the neighborhood of the connector 50. The first lead wire group 41G extended out from the multi-lumen tube 10 (first lumen 11) can thereby extend in the interior (inner hole of the first insulated tube 26) of the handle 20 without kinking.

The first lead wire group 41G extended out from the proximal end opening of the first insulated tube 26 is divided into 8 lead wires 41 making up this group, and each of these lead wires 41 is connected and fixed to each of the pin terminals arranged in the distal end surface 50A of the connector 50 with solder. Here, a region where the pin terminals (pin terminals 51), to which the lead wires 41 making up the first lead wire group 41G have been connected and fixed, are arranged is referred to as "a first terminal group region".

A distal end portion (portion about 10 mm long from the tip) of the second insulated tube 27 is inserted into the second lumen 12 of the multi-lumen tube 10, whereby the second insulated tube 27 is connected to the second lumen 12 into which the second lead wire group 42G extends.

The second insulated tube 27 connected to the second lumen. 12 passes through an inner hole of a second protecting tube 62 extending in the interior of the handle 20 and extends up to the neighborhood of the connector 50 (distal end surface 50A in which the pin terminals have been arranged) to form a passage through which the proximal end portion of the second lead wire group 42G is guided to the neighborhood of the connector 50. The second lead wire group 42G extended out from the multi-lumen tube 10 (second lumen 12) can thereby extend in the interior (inner hole of the second insulated tube 27) of the handle 20 without kinking.

The second lead wire group 42G extended out from the proximal end opening of the second insulated tube 27 is divided into 8 lead wires 42 making up this group, and each of these lead wires 42 is connected and fixed to each of the pin terminals arranged in the distal end surface 50A of the connector 50 with solder. Here, region where the pin terminals (pin terminals 52), to which the lead wires 42 making up the second lead wire group 42G have been connected and fixed, are arranged is referred to as "a second terminal group region".

A distal end portion (portion about 10 mm long from the tip) of the third insulated tube 28 is inserted into the third lumen 13 of the multi-lumen tube 10, whereby the third insulated tube 28 is connected to the third lumen 13 into which the third lead wire group 43G extends.

The third insulated tube 28 connected to the third lumen 13 passes through an inner hole of the second protecting tube 62 extending in the interior of the handle 20 and extends up to the neighborhood of the connector 50 (distal end surface 50A in which the pin terminals have been arranged) to form a passage through which the proximal end portion of the third lead wire group 43G is guided to the neighborhood of the connector 50. The third lead wire group 43G extended out from the multi-lumen tube 10 (third lumen 13) can thereby extend in the interior (inner hole of the third insulated tube 28) of the handle 20 without kinking.

The third lead wire group 43G extended out from the proximal end opening of the third insulated tube 28 is divided into 4 lead wires 43 making up this group, and each of these lead wires 43 is connected and fixed to each of the pin terminals arranged in the distal end surface 50A of the connector 50 with solder. Here, a region where the pin terminals (pin terminals 53), to which the lead wires 43 making up the third lead wire group 43G have been connected and fixed, are arranged is referred to as "a third terminal group region".

Here, as examples of materials forming the insulated tubes (first insulated tube 26, second insulated tube 27 and third insulated tube 28), may be mentioned polyimide resins, polyamide resins and polyamide-imide resins. Among these, the polyimide resins high in hardness, easy to insert the lead wire group therein and capable of forming a thin-wall tube are particularly preferred.

The wall thickness of each insulated tube is preferably 20 to 40 μm, and is 30 μm as a preferable example.

As examples of materials forming the protecting tubes (first protecting tube 61 and second protecting tube 62), into which the insulated tubes are respectively inserted, may be mentioned nylon-based elastomers such as "Pebax" (trademark, product of ARKEMA CO.).

According to the defibrillation catheter 100 of this embodiment having such a structure as described above, the first lead wire group 41G extends into the first insulated tube 26, the second lead wire group 42G extends into the second insulated tube 27, and the third lead wire group 43G extends into the third insulated tube 28, whereby the first lead wire group 41G, the second lead wire group 426 and the third lead wire group 43G can be completely insulated and isolated from one another even in the interior of the handle 20. As a result, short circuit (in particular, short circuit between lead wire groups extended out in the vicinity of the openings of the lumens) between the first lead wire group 41G, the second lead wire group 42G and the third lead wire group 43C in the interior of the handle 20 can be surely prevented when the voltage necessary for the defibrillation is applied.

In addition, in the interior of the handle 20, the first insulated tube 26 is protected by the first protecting tube 61, and the second insulated tube 27 and the third insulated tube 28 are protected by the second protecting tube 52, whereby the insulated tubes can be prevented from being damaged by, for example, contact or abrasion with a member (moving member) of the lug 22 upon a distal end deflection operation of the multi-lumen tube 10.

The defibrillation catheter 100 in this embodiment is equipped with a partition plate 55 for dividing the distal end surface 50A of the connector 50, in which the plurality of pin terminals have been arranged, into the first terminal group region, and the second and third terminal group regions and isolating the lead wires 41, and the lead wires 42 and the lead wires 43 from each other.

The partition plate 55 for dividing into the first terminal group region, and the second and third terminal group regions is obtained by molding an insulating resin into a gutter-like form having a flat surface at both sides. No particular limitation is imposed on the insulating resin forming the partition plate 55, and a general-purpose resin such as polyethylene may be used.

The thickness of the partition plate 55 is, for example, 0.1 to 0.5 mm, and is 0.2 mm as a preferable example.

The height (distance from a proximal end edge to a distal end edge) of the partition plate 55 requires to be higher than a clearance distance between the distal end surface 50A of the connector 50 and the insulated tubes (first insulated tube 26 and second insulated tube 27). When this clearance distance is 7 mm, the height is, for example, 8 mm. In a partition plate having a height less than 7 mm, its distal end edge cannot be located on a more distal end side than the proximal ends of the insulated tubes.

According to such a structure, the lead wires 41 (proximal end portions of the lead wires 41 extended out from the proximal end opening of the first insulated tube 26) making up the first lead wire group 41G and the lead wires 42 (proximal end portions of the lead wires 42 extended out from the proximal end opening of the second insulated tube 27) making up the second lead wire group 42G can be surely and orderly isolated from each other.

Unless the partition plate 55 is provided, the lead wires 41 and the lead wires 42 cannot be orderly isolated. (separated) from each other, and there is a possibility that these may be contacted.

The lead wires 41 making up the first lead wire group 41G and the lead wires 42 making up the second lead wire group 42G, to which voltages different in polarity from each other are respectively applied, are isolated from each other by the partition plate 55 without coming into contact with each other, so that short circuit does not occur between the first lead wire 41 (proximal end portion of the lead wire 41 extended out from the proximal end opening of the first insulated tube 26) making up the first lead wire group 41G and the lead wire 42 (proximal end portion of the lead wire 42 extended out from the proximal end opening of the second insulated tube 27) making up the second lead wire group 42G even when the voltage necessary for the intracardiac defibrillation is applied upon use of the defibrillation catheter 100.

In addition, when an error occurs when the lead wires are connected and fixed to the pin terminals upon production of the defibrillation catheter, for example, when a lead wire 41 making up the first lead wire group 41G is connected to a pin terminal in the second terminal group region, its lead wire 41 comes to cross the partition plate 55, so that an error in connection can be easily found.

Incidentally, the lead wires 43 (pin terminals 53) making up the third lead wire group 43G are isolated together with the lead wires 42 (pin terminals 52) from the lead wires 41 (pin terminals 51) by the partition plate 55. However, the structure is not limited thereto, and the lead wires 43 (pin terminals 53) may also be isolated together with the lead wires 41 (pin terminals 51) from the lead wires 42 (pin terminals 52) by the partition plate 55.

In the defibrillation catheter 100, the distal end edge of the partition plate 55 is located on a more distal end side than either of the proximal end of the first insulated tube 26 and the proximal end of the second insulated tube 27.

The partition plate 55 thereby comes to be always present between the lead wires (first lead wires 41 making up the first lead wire group 41G) extended out from the proximal end opening of the first insulated tube 26 and the lead wires (lead wires 42 making up the second lead wire group 42G) extended out from the proximal end opening of the second insulated tube 27, so that short circuit caused by contact between the lead wire 41 and the lead wire 42 can be surely prevented.

As illustrated in FIG. 8, the 8 lead wires 41 extended out from the proximal end opening of the first insulated tube 26 and connected and fixed to the pin terminals 51 of the connector 50, the 8 lead wires 42 extended out from the proximal end opening of the second insulated tube 27 and connected and fixed to the pin terminals 52 of the connector 50, and the 4 lead wires 43 extended out from the proximal end opening of the third insulated tube 28 and connected and fixed to the pin terminals 53 of the connector 50 retain and fix their forms by strengthening (setting) their peripheries with a resin 58.

The resin 58 retaining the forms of the lead wires is formed into a cylindrical form having the same diameter as the connector 50, and the pin terminals, the lead wires, the proximal end portions of the insulated tubes and the partition plate 55 are filled into the interior of this resin formed body.

According to the structure that the proximal end portions of the insulated tubes are filled into the interior of the resin formed body, the whole regions of the lead wires (proximal end portions) extended out from the proximal end openings of the insulated tubes and connected and fixed to the pin terminals can be completely covered with the resin 58 to completely retain and fix the forms of the lead wires (proximal end portions).

In addition, the height (distance from a proximal end surface to a distal end surface) of the resin formed body is preferably higher than the height of the partition plate 55. When the height of the partition plate 55 is 8 mm, its height is, for example, 9 mm.

Here, no particular limitation is imposed on the resin 58 forming the resin formed body. However, a thermosetting resin or photo-setting resin is preferably used. As specific examples thereof, may be mentioned urethane-based, epoxy-based and urethane-epoxy-based setting resins.

According to such a structure as described above, the forms of the lead wires are retained and fixed by the resin 58, so that the lead wires extended out from the proximal end openings of the insulated tubes can be prevented from being damaged (for example, causing cracks in a coating resin of the lead wires) by their kinking or contact with an edge of the pin terminal upon production of the defibrillation catheter 100 (upon installation of the connector 50 in the interior of the handle 20).

As illustrated in FIG. 1, the power source device 700 making up the catheter system according to this embodiment is equipped with a DC power source unit 71, a catheter-connected connector 72, an electrocardiograph-connected connector 73, an external switch (input means) 74, an arithmetic processing unit 75, a changeover unit 76, an electrocardiogram input connector 77, and a display means 78.

A capacitor is built in the DC power source unit 71, and the built-in capacitor is charged by input of the external switch 74 (charging switch 743).

The catheter-connected connector 72 is connected to the connector 50 of the defibrillation catheter 100 and electrically connected to proximal sides of the first lead wire group (41G), the second lead wire group (42G) and the third lead wire group (43G).

Figure 9:
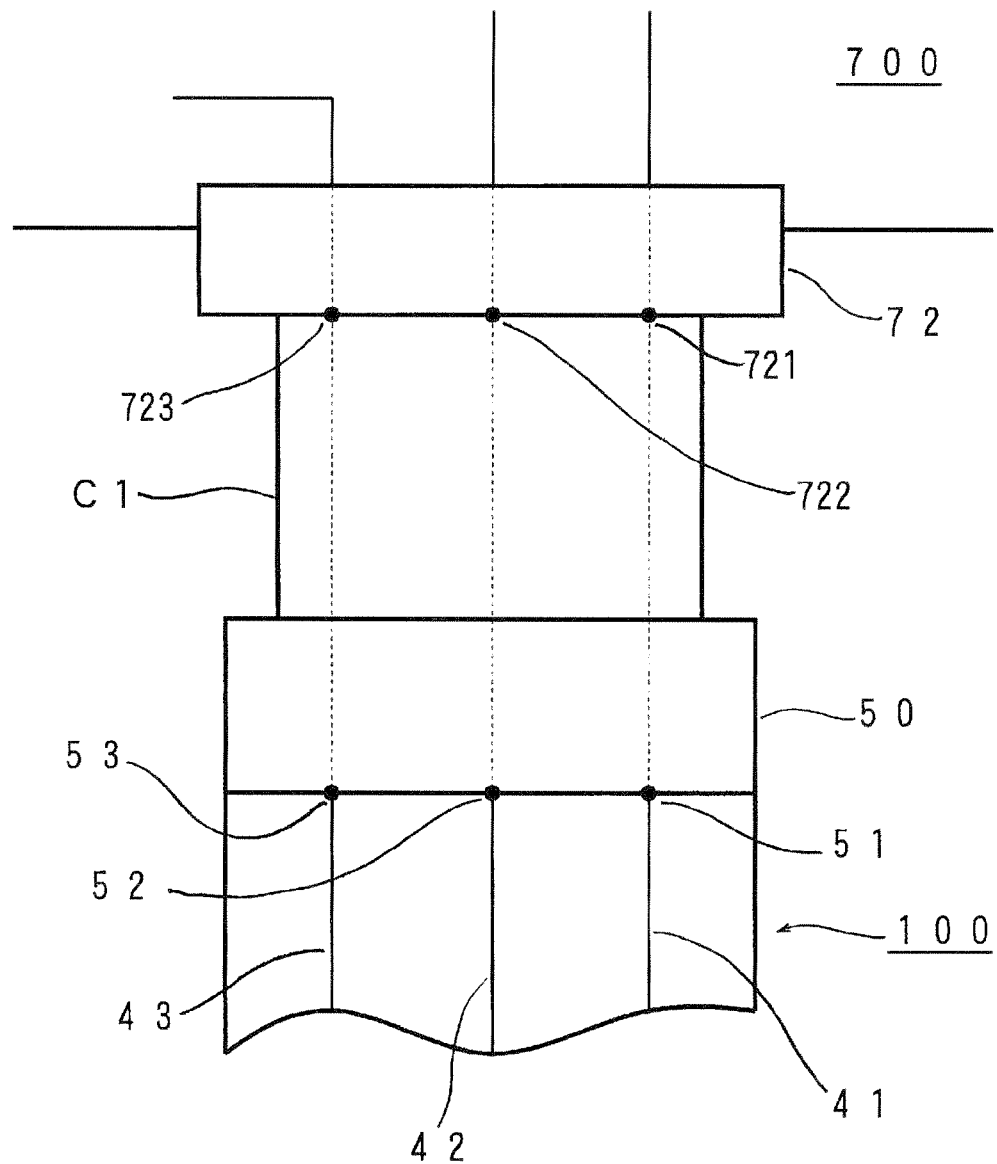
[FIG. 9] is an explanatory view typically illustrating a connected state between a connector of the defibrillation catheter and a catheter-connected connector of a power source device in the catheter system illustrated in FIG. 1.

As illustrated in FIG. 9, the connector 50 of the defibrillation catheter 100 is connected to the catheter-connected connector 72 of the power source device 700 by a connector cable C1, thereby respectively connecting the pin terminals 51 (actually, 8 terminals), to which the 8 lead wires 41 making up the first lead wire group have been connected and fixed, to terminals 721 (actually, 8 terminals) of the catheter-connected connector 72, the pin terminals 52 (actually, 8 terminals), to which the 8 lead wires 42 making up the second lead wire group have been connected and fixed, to terminals 722 (actually, 8 terminals) of the catheter-connected connector 72, and the pin terminals 53 (actually, 4 terminals), to which the 4 lead wires 43 making up the third lead wire group have been connected and fixed, to terminals 723 (actually, 4 terminals) of the catheter-connected connector 72.

Here, the terminals 721 and terminals 722 of catheter-connected connector 72 are connected to the changeover unit 76, and the terminals 723 are directly connected to the electrocardiograph-connected connector 73 without going through the changeover unit 76.

The cardiac potential information measured by the first DC electrode group 31C and the second DC electrode group 32G thereby reaches the electrocardiograph-connected connector 73 via the changeover unit 76, and the cardiac potential information measured by the potential-measuring electrode group 33G reaches the electrocardiograph-connected connector 73 without going through the changeover unit 76.

The electrocardiograph-connected connector 73 is connected to an input terminal of an electrocardiograph 800.

The external switch 74 that is an input means is composed of a mode changing-over switch 741 for changing over a cardiac potential measuring mode and a defibrillation mode each other, an application energy setting switch 742 for setting electric energy to be applied upon defibrillation, a charging switch 743 for charging the DC power source unit 71, and an energy-applying switch (discharging switch) 744 for applying energy to conduct defibrillation. All input signals from these external switches 74 are send to the arithmetic processing unit 75.

The arithmetic processing unit 75 controls the DC power source unit 71, the changeover unit 76 and the display means 78 based on input of the external switch 74.

This arithmetic processing unit 75 has an output circuit 751 for outputting direct current voltages from the DC power source unit 71 to the electrodes of the defibrillation catheter 100 via the changeover unit 76.

By this output circuit 751, the direct current voltages can be applied in such a manner that the terminals 721 (finally, the first DC electrode group 31G of the defibrillation catheter 100) of the catheter-connected connector 72 illustrated in FIG. 9 and the terminals 722 (finally, the second DC electrode group 32G of the defibrillation catheter 100) of the catheter-connected connector 72 become polarities opposite to each other (when one electrode group becomes a minus pole, the other electrode group becomes a plus pole).

The changeover unit 76 is composed of a changeover switch of two contacts per circuit, in which the catheter-connected connector 72 (terminals 721 and terminals 722) is connected to a common contact, the electrocardiograph-connected connector 73 is connected to a first contact, and the arithmetic processing unit 75 is connected to a second contact.

In other words, when the first contact is selected, a route linking the catheter-connected connector 72 to the electrocardiograph-connected connector 73 is ensured, while when the second contact is selected, a route linking the catheter-connected connector 72 to the arithmetic processing unit 75 is ensured.

The changeover operation of the changeover unit 76 is controlled by the arithmetic processing unit 75 based on the input of the external switch 74 (mode changing-over switch 741 or energy-applying switch 744).

The electrocardiogram input connector 77 is connected to the arithmetic processing unit 75 and also to an output terminal of the electrocardiograph 800.

By this electrocardiogram input connector 77, the cardiac potential information (ordinarily, a part of the cardiac potential information inputted into the electrocardiograph 800) outputted from the electrocardiograph 800 can be inputted into the arithmetic processing unit 75, and the DC power source unit 71 and the changeover unit 76 can be controlled on the basis of this the cardiac potential information in the arithmetic processing unit 75.

The display means 78 is connected to the arithmetic processing unit 75 and displays the cardiac potential information (mainly, cardiac potential waveform) inputted into the arithmetic processing unit 75 from the electrocardiogram input connector 77 thereon, so that an operator can conduct a defibrillation treatment (for example, input of the external switch) while monitoring the cardiac potential information (waveform) inputted into the arithmetic processing unit 75.

The electrocardiograph 800 (input terminal) making up the catheter system according to this embodiment is connected to the electrocardiograph-connected connector 73 of the power source device 700, and the cardiac potential information measured by the defibrillation catheter 100 (electrodes making up the first DC electrode group 31G, the second DC electrode group 32G and the proximal-side potential-measuring electrode group 33G) is inputted into the electrocardiograph 800 from the electrocardiograph-connected connector 73.

In addition, the electrocardiograph 800 (another input terminal) is also connected to a cardiac potential-measuring means 900, and the cardiac potential information measured by the cardiac potential-measuring means 900 is also inputted into the electrocardiograph 800.

Here, as examples of the cardiac potential-measuring means 900, may be mentioned an electrode pad attached to the body surface of a patient to measure a 12-lead electrocardiogram, and an electrode catheter (another electrode catheter than the defibrillation catheter 100) installed in a heart of a patient.

The electrocardiograph 800 (output terminal) is connected to the electrocardiogram input connector 77 of the power source device 700 and can send a part of the cardiac potential information (the cardiac potential information from the defibrillation catheter 100 and the cardiac potential information from the cardiac potential-measuring means 900) inputted into the electrocardiograph 800 to the arithmetic processing unit 75 from the electrocardiogram input connector 77.

The defibrillation catheter 100 in this embodiment can be used as an electrode catheter for cardiac potential measurement when a defibrillation treatment is not necessary.

Figure 10:
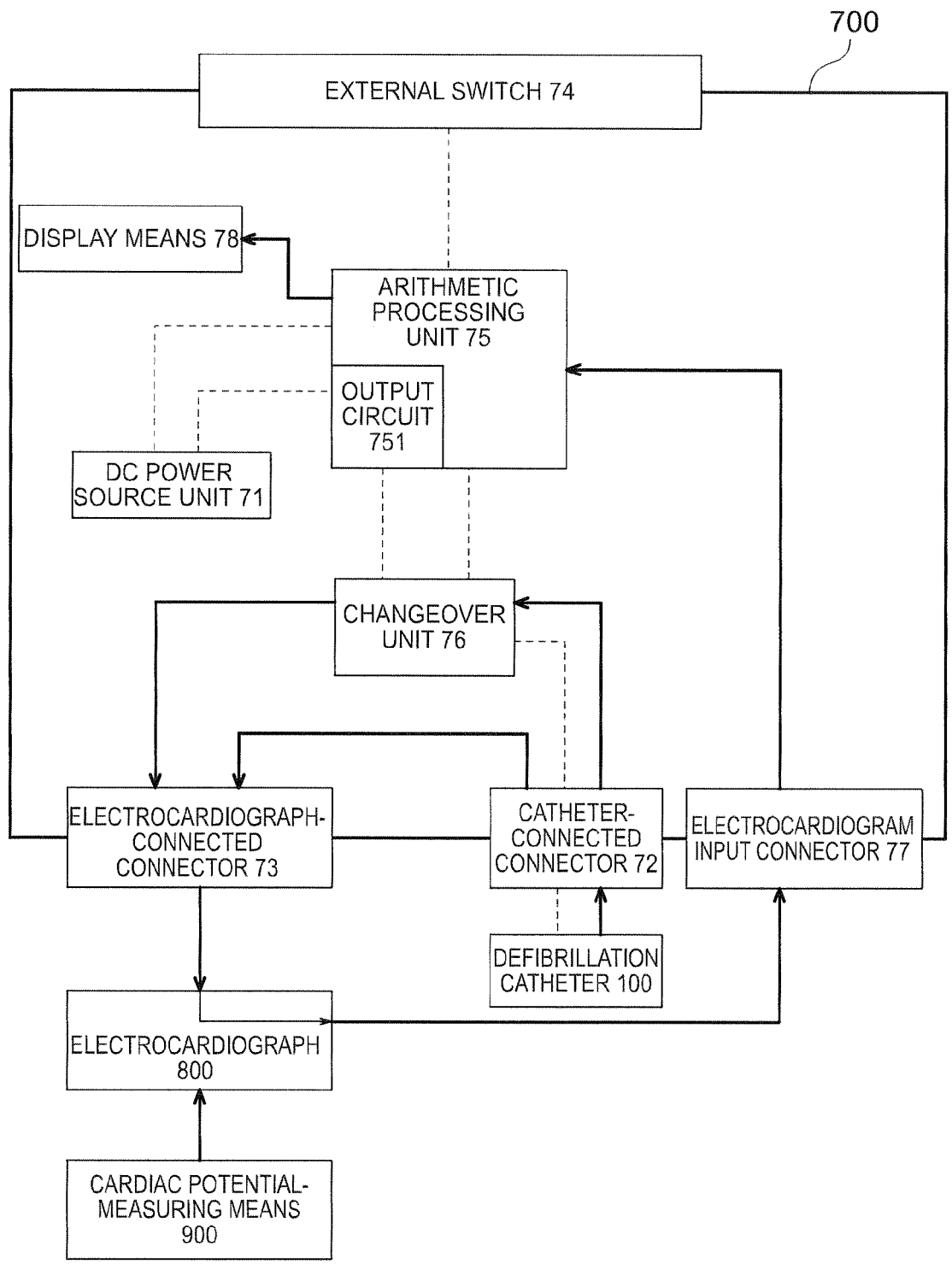
[FIG. 10] is a block diagram illustrating the flow of cardiac potential information when a cardiac potential is measured by the defibrillation catheter in the catheter system illustrated in FIG. 1.

FIG. 10 illustrates the flow of cardiac potential information when a cardiac potential is measured by the defibrillation catheter 100 according to this embodiment upon conducting cardiac catheterization (for example, a high frequency treatment).

At this time, the changeover unit 76 of the power source device 700 selects the first contact connected to the electrocardiograph-connected connector 73.

The cardiac potential measured by the electrodes making up the first DC electrode group 31G and/or the second DC electrode group 32G of the defibrillation catheter 100 is inputted into the electrocardiograph 800 via the catheter-connected connector 72, the changeover unit 76 and the electrocardiograph-connected connector 73.

In addition, the cardiac potential measured by the electrodes making up the proximal-side potential-measuring electrode group 33G is inputted into the electrocardiograph 800 directly via the electrocardiograph-connected connector 73 from the catheter-connected connector 72 without going through the changeover unit 76.

The cardiac potential information (cardiac potential waveform) from the defibrillation catheter 100 is displayed on a monitor (not illustrated) of the electrocardiograph 800.

In addition, a part (for example, a potential difference between electrodes 31 (a first electrode and a second electrode) making up the first DC electrode group 31G) of the cardiac potential information from the defibrillation catheter 100 can be inputted into the display means 78 via the electrocardiogram input connector 77 and the arithmetic processing unit 75 from the electrocardiograph 800 and displayed thereon.

As described above, the defibrillation catheter 100 can be used as an electrode catheter for cardiac potential measurement when a defibrillation treatment is riot necessary during cardiac catheterization.

And now, when atrial fibrillation has occurred during cardiac catheterization, a defibrillation treatment can be immediately conducted by the defibrillation catheter 100 which was used as the electrode catheter. As a result, such troubles as to newly insert a catheter for defibrillation when atrial fibrillation has occurred can be saved.

An exemplary defibrillation treatment by the intracardiac defibrillation catheter system according to this embodiment will hereinafter be described according to the flow chart illustrated in FIG. 11.

Figure 11A:
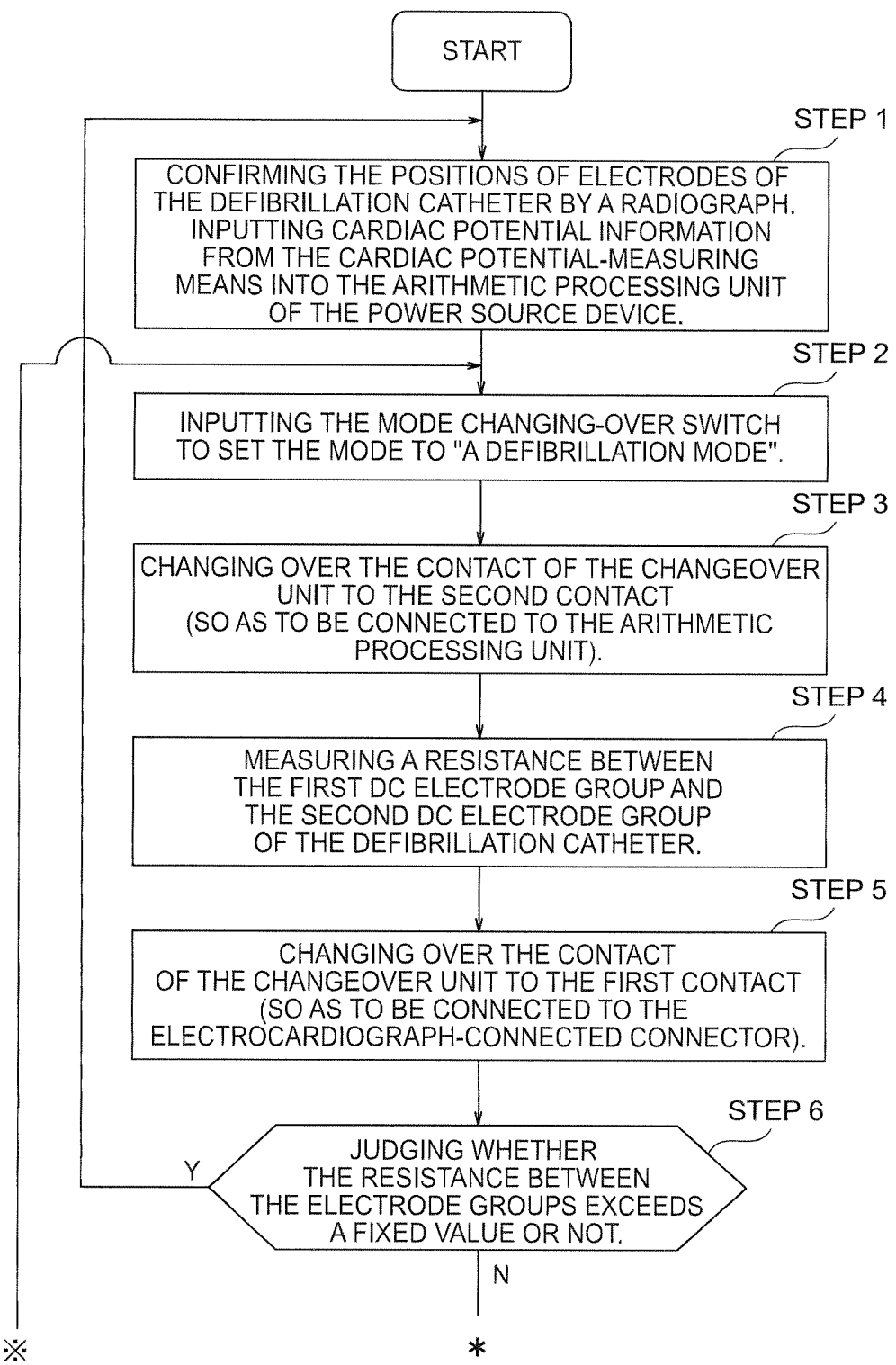
[FIG. 11A] is a part (Step 1 to Step 6) of a flow chart illustrating the action and operation of a power source device in the catheter system illustrated in FIG. 1.
Figure 12:
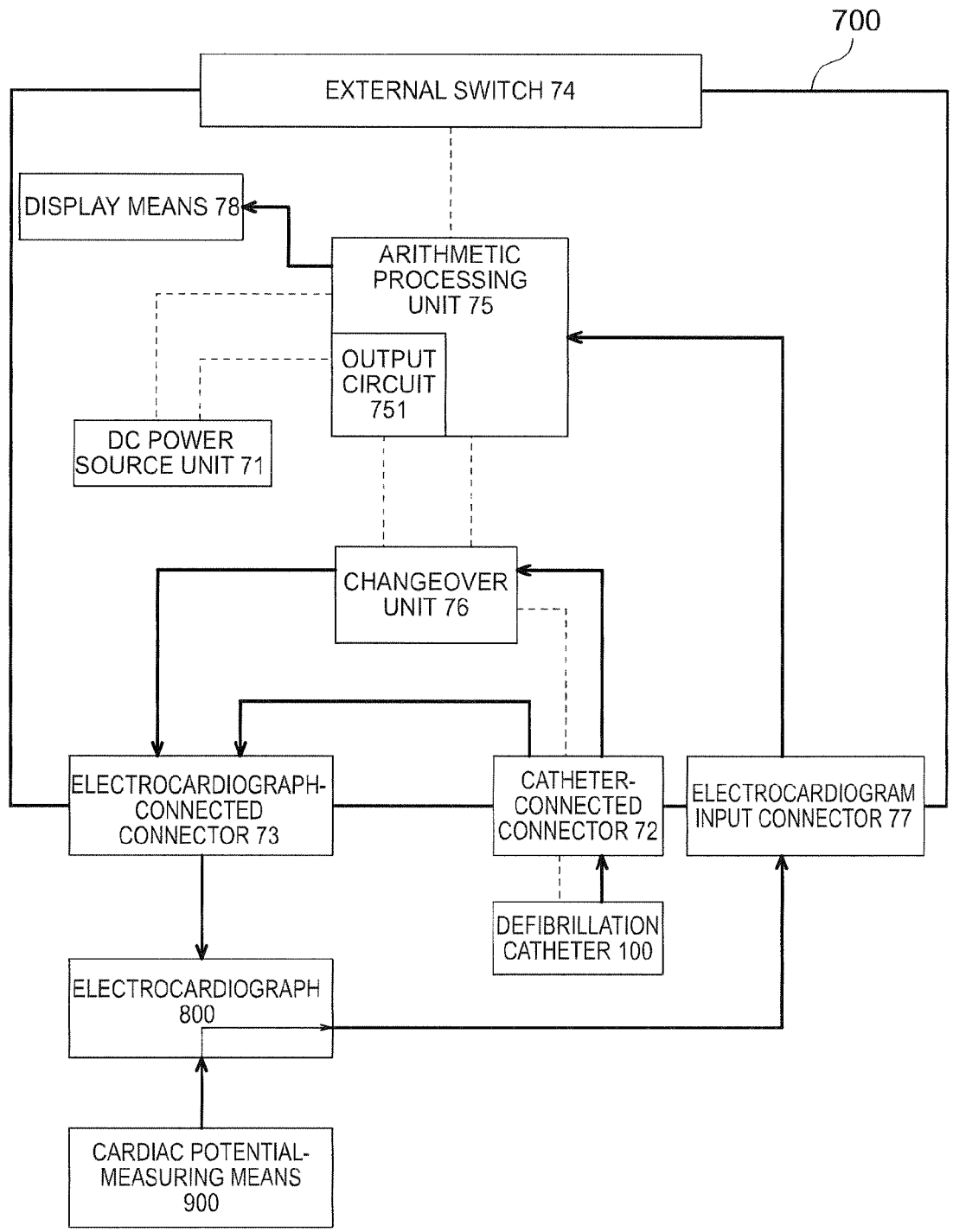
[FIG. 12] is a block diagram illustrating the flow of cardiac potential information in a cardiac potential measuring mode in the catheter system illustrated in FIG. 1.

(1) First, the positions of the electrodes (electrodes making up the first DC electrode group 31G, the second DC electrode group 32G and the proximal-side potential-measuring electrode group 33G) of the defibrillation catheter 100 are confirmed by a radiograph, and a part of cardiac potential information (12-lead electrocardiogram) inputted into the electrocardiograph 800 from the cardiac potential-measuring means 900 (electrode pad attached to the body surface) is selected and inputted into the arithmetic processing unit 75 of the power source device 700 from the electrocardiogram input connector 77 (Step 1 in FIG. 11A). At this time, the part of the cardiac potential information inputted into the arithmetic processing unit 75 is displayed on the display means 78 (see FIG. 12).

In addition, cardiac potential information inputted into the electrocardiograph 800 via the catheter-connected connector 72, the changeover unit 76 and the electrocardiograph-connected connector 73 from the electrodes making up the first DC electrode group 31G and/or the second DC electrode group 32G of the defibrillation catheter 100, and cardiac potential information inputted into the electrocardiograph 800 via the catheter-connected connector 72 and the electrocardiograph-connected connector 73 from the electrodes making up the proximal-side potential-measuring electrode group 33G of the defibrillation catheter 100 are displayed on a monitor (not illustrated) of the electrocardiograph 800.

(2) Then, the mode changing-over switch 741 that is the external switch 74 is inputted. The power source device 700 in this embodiment is set to "a cardiac potential measuring mode" in an initial state, and the changeover unit 76 selects the first contact to ensure a route from the catheter-connected connector 72 to the electrocardiograph-connected connector 73 via the changeover unit 76.

The mode changing-over switch 741 is inputted, whereby the mode is set to "a defibrillation mode" (Step 2).

Figure 13:
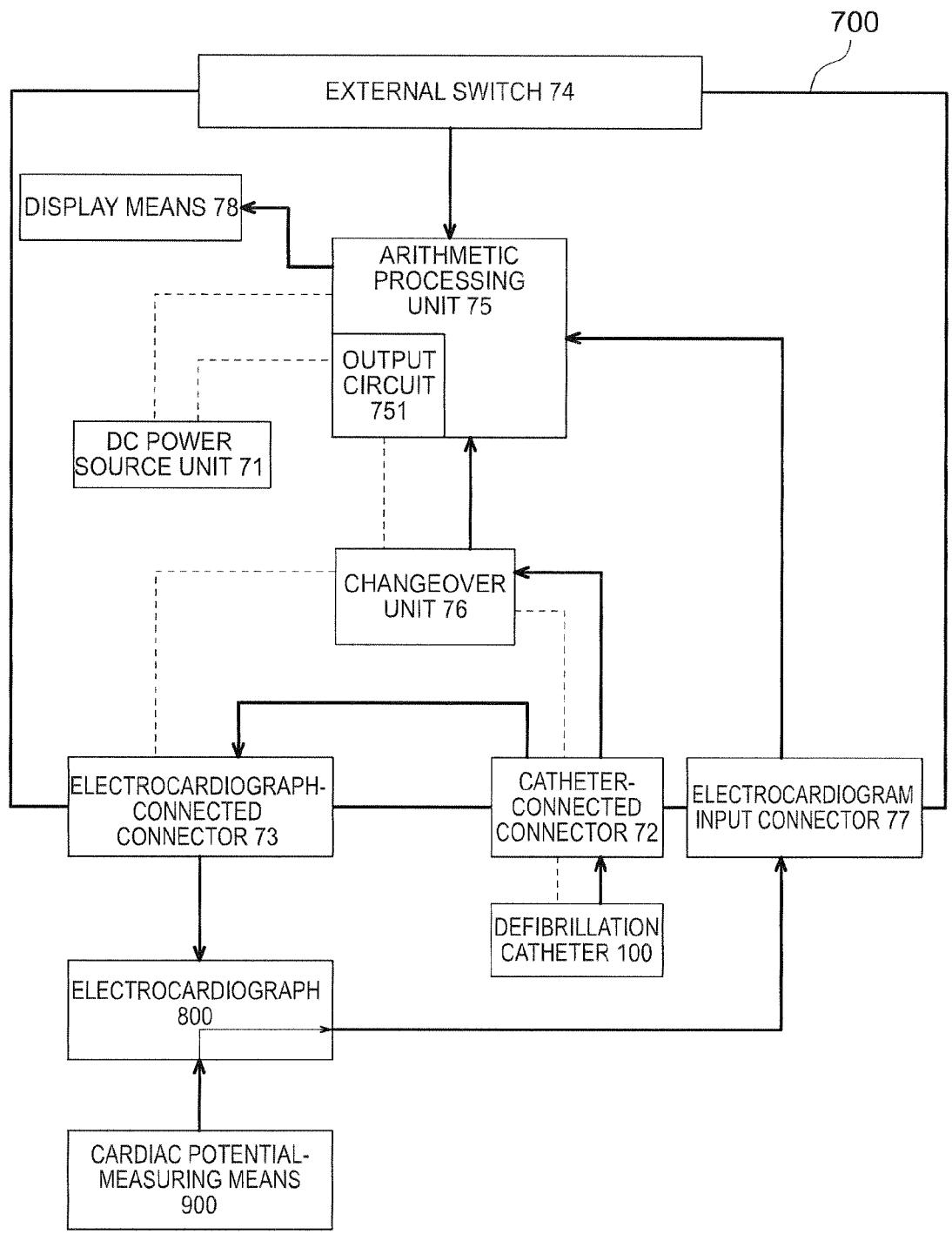
[FIG. 13] is a block diagram illustrating the flow of information as to a measured value of a resistance between electrode groups and cardiac potential information in a defibrillation mode in the catheter system illustrated in FIG. 1.

(3) When the mode is changed over to the defibrillation mode by inputting the mode changing-over switch 741 as illustrated in FIG. 13, the contact of the changeover unit 76 is changed over to the second contact according to a control signal from the arithmetic processing unit 75 to ensure a route from the catheter-connected connector 72 to the arithmetic processing unit 75 via the changeover unit 76 and interrupt the route from the catheter-connected connector 72 to the electrocardiograph-connected connector 73 via the changeover unit 76 (Step 3). At the time the changeover unit 76 selects the second contact, cardiac potential information from the electrodes making up the first DC electrode group 31G and the second DC electrode group 32G of the defibrillation catheter 100 cannot be inputted into the electrocardiograph 800 (thus, this cardiac potential information cannot be sent to the arithmetic processing unit 75). However, cardiac potential information from the electrodes making up the proximal-side potential-measuring electrode group 33G, which does not go through the changeover unit 76, is inputted into the electrocardiograph 800.

(4) At the time the contact of the changeover unit 76 has been changed over to the second contact, a resistance between the first DC electrode group (31G) and the second DC electrode group (32G) of the defibrillation catheter 100 is measured (Step 4). The resistance value inputted into the arithmetic processing unit 75 from the catheter-connected connector 72 via the changeover unit 76 is displayed together with a part of the cardiac potential information inputted into the arithmetic processing unit 75 from the cardiac potential-measuring means 900 on the display means 78 (see FIG. 13).

(5) The contact of the changeover unit 76 is changed over to the first contact, whereby the route is returned to the route from the catheter-connected connector 72 to the electrocardiograph-connected connector 73 via the changeover unit 76 (Step 5).

Incidentally, the time (from Step 3 to Step 5) for which the changeover unit 76 selects the second contact is, for example, 1 second.

(6) The arithmetic processing unit 75 judges whether the resistance measured in Step 4 exceeds a fixed value or not, so as to proceed to the next Step 7 (provision for applying a direct current voltage) when the resistance does not exceed the fixed value, or to return to Step 1 (the confirmation of the positions of the electrodes of the defibrillation catheter 100) when the resistance exceeds the fixed value (Step 6).

Here, the fact that the resistance exceeds the fixed value means that the first DC electrode group 31G and/or the second DC electrode group 32G are not brought into sure contact with the respective predetermined sites (for example, a vessel wall of the coronary vein and an inner wall of the right atrium), so that the step must be returned to Step 1 to readjust the positions of the electrodes.

As described above, voltages can be applied only when the first DC electrode group and the second DC electrode group of the defibrillation catheter 100 have been brought into sure contact with the respective predetermined sites (for example, a vessel wall of the coronary vein and an inner wall of the right atrium), so that the defibrillation treatment can be effectively conducted.

Figure 11B:
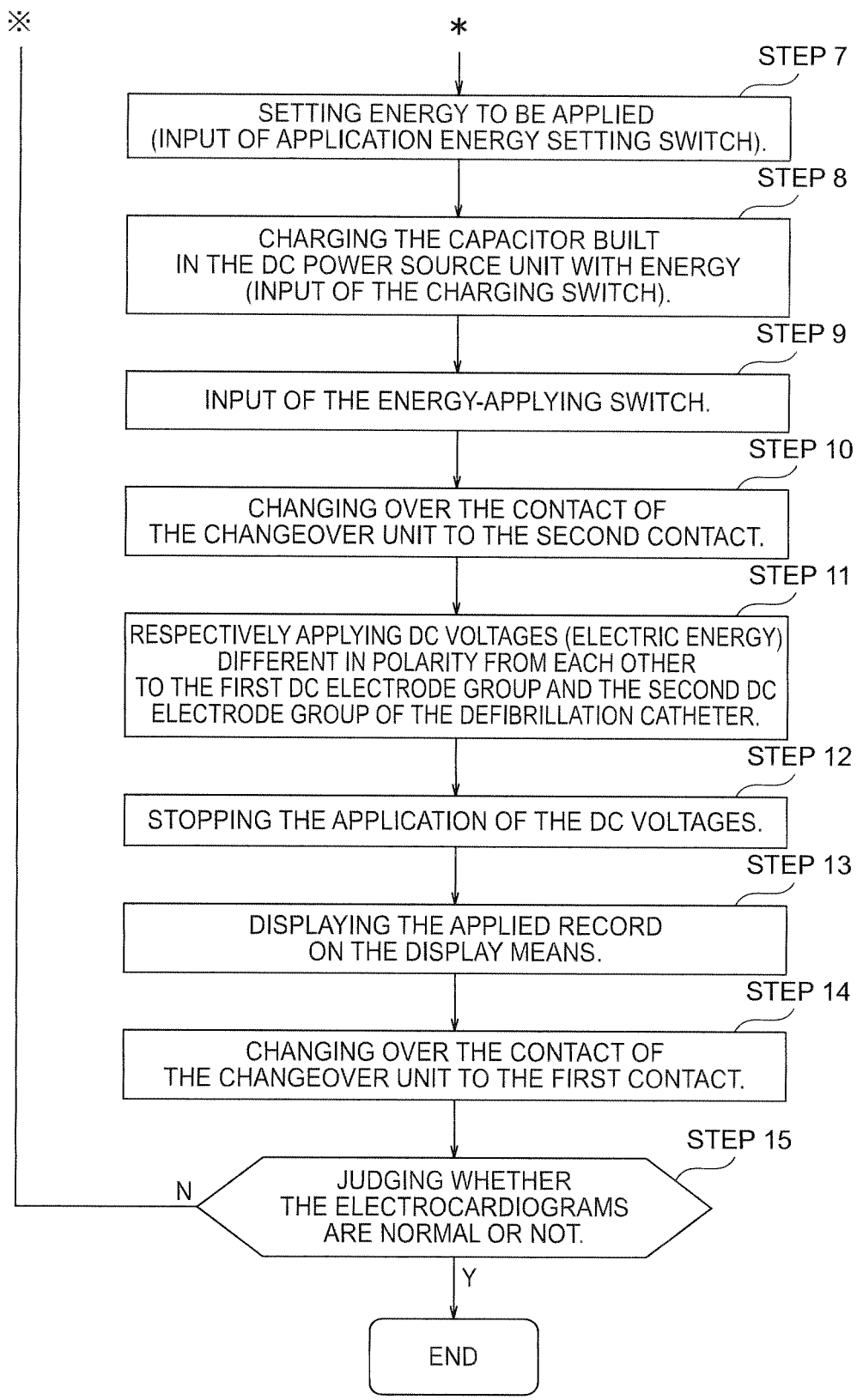
[FIG. 11B] is the remainder (Step 7 to Step 15) of the flow chart illustrating the action and operation of the power source device in the catheter system illustrated in FIG. 1.

(7) The application energy setting switch 742 that is the external stitch 74 is inputted to set energy to be applied upon defibrillation (Step 7 in FIG. 11B).

According to the electrode device 700 of this embodiment, the energy to be applied can be set every 1 J from 1 J to 30 J.

(8) The charging switch 743 that is the external stitch 74 is inputted to charge the capacitor built in the DC power source unit 71 with energy (Step 8).

(9) The energy-applying switch 744 that is the external switch 74 is inputted after completion of the charging (Step 9).

(10) When the energy-applying switch 744 is inputted, the contact of the changeover unit 76 is changed over to the second contact by the arithmetic processing unit 75 to ensure a route from the catheter-connected connector 72 to the arithmetic processing unit 75 via the changeover unit 76 and interrupt the route from the catheter-connected connector 72 to the electrocardiograph-connected connector 73 via the changeover unit 76 (Step 10).

Figure 14:
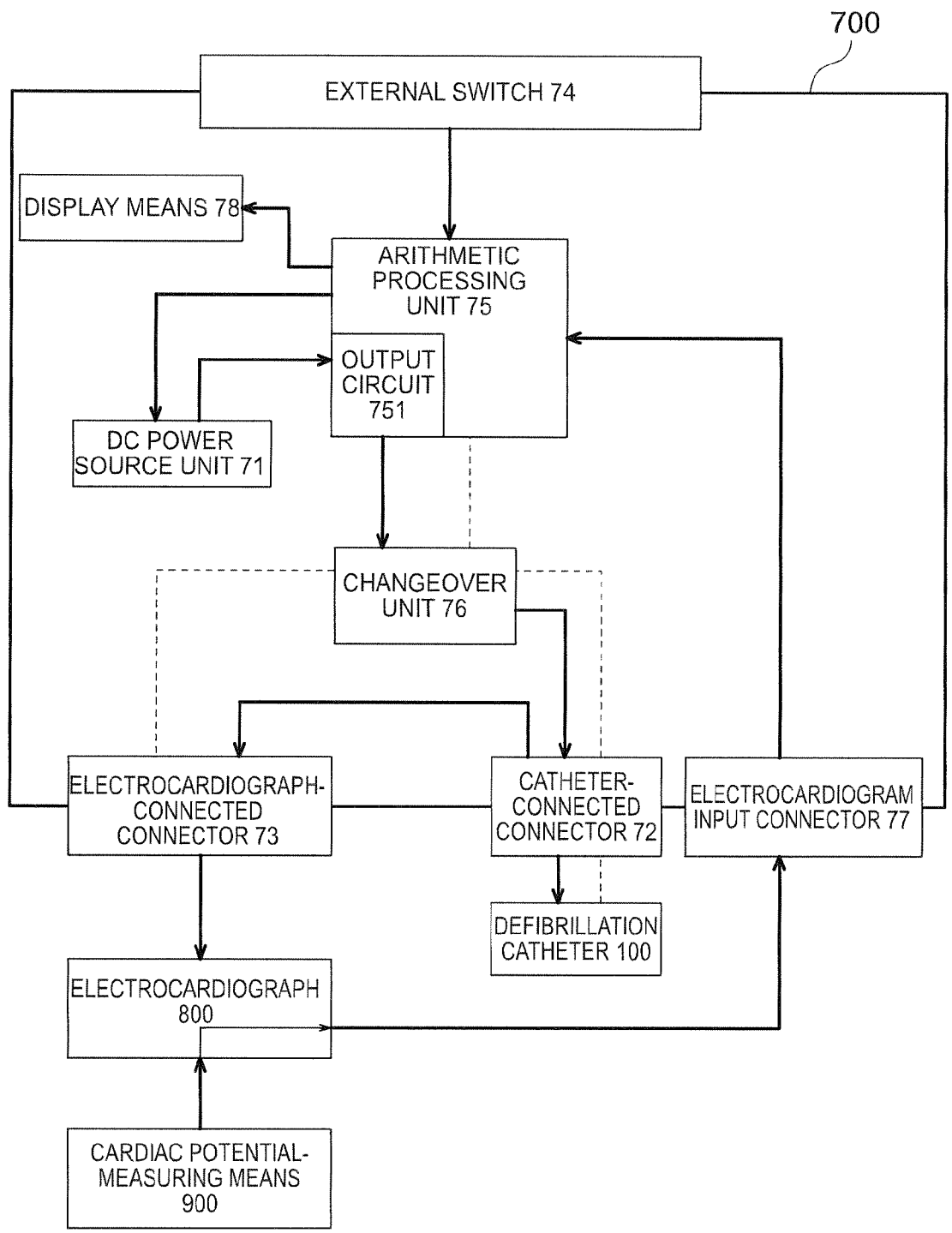
[FIG. 14] is a block diagram illustrating a state at the time a direct current voltage has been applied in a defibrillation mode in the catheter system illustrated in FIG. 1.

(11) After the contact of the changeover unit 76 is changed over to the second contact, direct current voltages different in polarity from each other are respectively applied to the first DC electrode group and the second DC electrode group of the defibrillation catheter 100 via the output circuit of the arithmetic processing unit 75, the changeover unit 76 and the catheter-connected connector 72 from the DC power source unit 71 which has received a control signal from the arithmetic processing unit 75 (Step, 11, see FIG. 14).

Here, the arithmetic processing unit 75 conducts arithmetic processing so as to apply the voltages synchronizing with the cardiac potential waveform inputted via the electrocardiogram input connector 77 to send the DC power source unit 71 a control signal.

Specifically, one R wave (maximum peak) is detected in the cardiac potential waveform (a part of the 12-lead electrocardiogram from the cardiac potential-measuring means 900) successively inputted into the arithmetic processing unit 75 to find its peak height, and application of the voltages is then started after a fixed time (for example, an extremely short time of about 1/10 of a peak width of the R wave) has elapsed from a point of time (time the next R wave has built up) a potential difference has reached 80% (trigger level) of this peak height.

Figure 15:
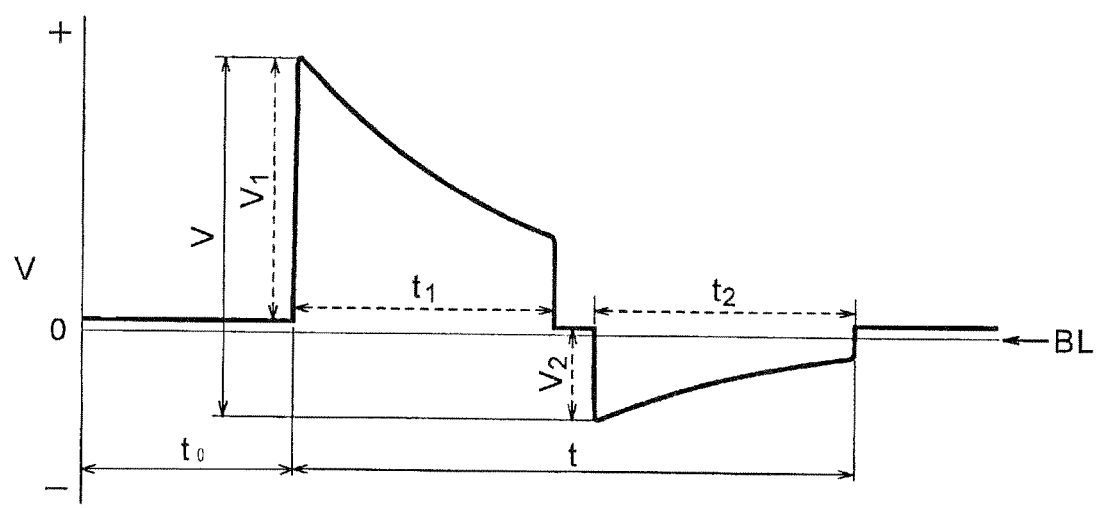
[FIG. 15] is a potential waveform diagram measured when predetermined electric energy has been applied by the defibrillation catheter making up the catheter system illustrated in FIG. 1.

FIG. 15 illustrates a potential waveform measured when predetermined electric energy (for example, set output—10 J) has been applied by the defibrillation catheter 100 in this embodiment. In this drawing, an axis of abscissa and an axis of ordinate indicate a time and a potential, respectively.

First, after a fixed time ($t_0$) has elapsed from the time a potential difference in the cardiac potential waveform inputted into the arithmetic processing unit 75 reached a trigger level, a direct current voltage is applied between the first DC electrode group 31G and the second DC electrode group 32G in such a manner that the first DC electrode group 31G becomes a minus pole and the second DC electrode group 32G becomes a plus pole, whereby electric energy is supplied to build up a measuring potential ($V_1$ is a peak voltage at this time). After a fixed time ($t_1$) has elapsed, a direct current voltage that the poles have been reversed in such a manner that the first DC electrode group 31G becomes a plus pole and the second DC electrode group 32G becomes a minus pole is applied between both electrode groups, whereby electric energy is supplied to build up a measuring potential ($V_2$ is a peak voltage at this time).

Here, the time ($t_0$) from the time the trigger level has been reached to the time the application is started is, for example, 0.01 to 0.05 seconds, and is 0.01 seconds as a preferable example, and the time ($t=t_1+t_2$) is, for example, 0.006 to 0.03 seconds, and is 0.02 seconds as a preferable example.

The voltage can be thereby applied synchronizing with the cardiac potential waveform (R wave that is the maximum peak) inputted into the arithmetic processing unit 75, and so a defibrillation treatment can be effectively conducted.

The peak voltage ($V_1$) measured is, for example, 300 to 600 V.

(12) After a fixed time ($t_0+t_1$) has elapsed from the time the potential difference in the cardiac potential waveform reached the trigger level, the application of the voltage from the DC power source unit 71 is stopped by receiving a control signal from the arithmetic processing unit 75 (Step 12).

(13) After the application of the voltage has been stopped, the applied record (such a cardiac potential waveform upon the application as illustrated in FIG. 15) is displayed on the display means 78 (Step 13). The time displayed is, for example, 5 seconds.

(14) The contact of the changeover unit 76 is changed over to the first contact, whereby the route is returned to the route from the catheter-connected connector 72 to the electrocardiograph-connected connector 73 via the changeover unit 76 to input the cardiac potential information from the electrodes making up the first DC electrode group 31G and the second DC electrode group 32G of the defibrillation catheter 100 into the electrocardiograph 800 (Step 14).

(15) The cardiac potential information (electrocardiogram) from the electrodes (electrodes making up the first DC electrode group 31G, the second DC electrode group 32G and the proximal-side potential-measuring electrode group 33G) making up the defibrillation catheter 100, and the cardiac potential information (12-lead electrocardiogram) from the cardiac potential-measuring means 900, which are displayed on the monitor of the electrocardiograph 800, are observed to complete the operation if "normal" or return the step to Step 2 if "not normal (atrial fibrillation is not cured)" (Step 15).

According to the catheter system of this embodiment, electric energy is directly given to a heart that has suffered fibrillation by the first DC electrode group 31G and the second DC electrode group 32G of the defibrillation catheter 100, whereby electric stimulus (electric shock) necessary and sufficient for defibrillation treatment can be surely given only to the heart.

In addition, no burn is caused on the body surface of the patient because the electric energy can be directly applied to the heart.

Further, since the cardiac potential information measured by the electrodes 33 making up the proximal-side potential-measuring electrode group 33G is inputted into the electrocardiograph 800 via the electrocardiograph-connected connector 73 from the catheter-connected connector 72 without going through the changeover unit 76, and the cardiac potential-measuring means 900 is connected to this electrocardiograph 800, the electrocardiograph 800 can acquired the cardiac potential information measured by the proximal-side potential-measuring electrode group 33G and the cardiac potential-measuring means 900 even upon defibrillation treatment (when the contact of the changeover unit 76 is changed over to the second contact to interrupt the route from the catheter-connected connector 72 to the electrocardiograph-connected connector 73 via the changeover unit 76) during which the electrocardiograph 800 cannot acquire the cardiac potential from the first DC electrode group 31G and the second DC electrode group 32G of the defibrillation catheter 100, so that the defibrillation treatment can be conducted while monitoring the cardiac potential in the electrocardiograph 800.

Furthermore, the arithmetic processing unit 75 of the power source device 700 conducts arithmetic processing so as to apply voltages synchronizing with the cardiac potential waveform inputted via the electrocardiogram input connector 77 to control the DC power source unit 71 (the application of the voltages is started after a fixed time (for example, 0.01 seconds) has elapsed from the time a potential difference in the cardiac potential waveform reached a trigger level), so that the voltages can be applied to the first DC electrode group 31G and the second DC electrode group 32G of the defibrillation catheter 100 synchronizing with the cardiac potential waveform to effectively conduct the defibrillation treatment.

In addition, the arithmetic processing unit 75 controls the DC power source unit so as to be ready to apply direct current voltages only when the resistance between the electrode groups of the defibrillation catheter 100 does not exceed the fixed value, i.e., when the first DC electrode group 31G and the second DC electrode group 32G have been brought into sure contact with the respective predetermined sites (for example, a vessel wall of the coronary vein and an inner wall of the right atrium), so that the defibrillation treatment can be effectively conducted.

<Second Embodiment>

Figure 16:
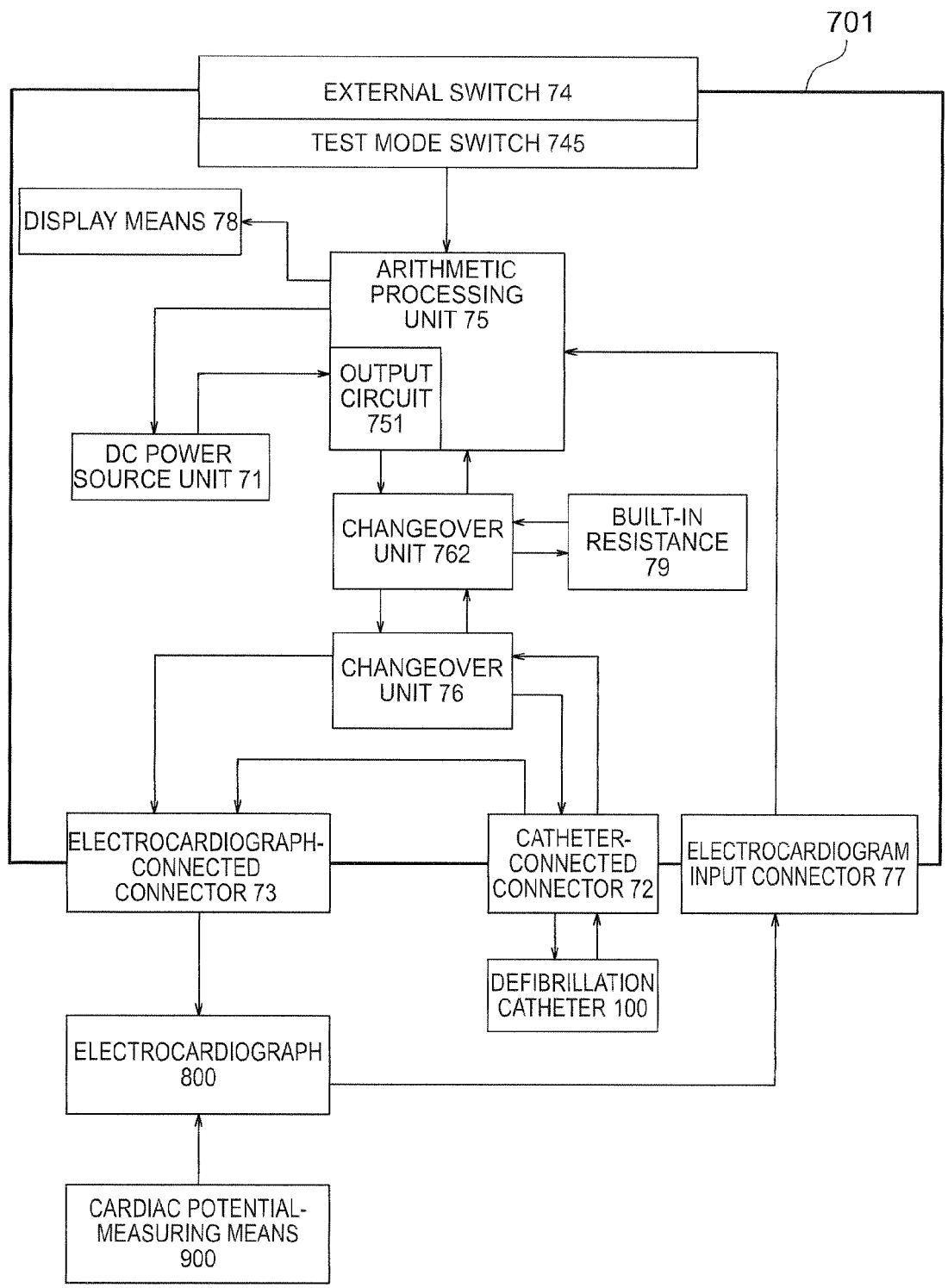
[FIG. 16] is a block diagram illustrating another embodiment of the intracardiac defibrillation catheter system according to the present invention.

FIG. 16 is a block diagram illustrating another embodiment of the intracardiac defibrillation catheter system according to the present invention.

A power source device 701 in this embodiment is provided with a built-in resistance 79 having an already known resistance value and a changeover unit 762 to which this built-in resistance 79 is connected, in addition to the structure of the power source device 700 in the first embodiment, and a test mode switch 745 is provided as an external switch 74.

The changeover unit 762 is composed of a changeover switch of two contacts per circuit, in which the arithmetic processing unit 75 is connected to a common contact, the changeover unit 76 is connected to a first contact, and the built-in resistance 79 is connected to a second contact.

In other words, when the first contact is selected, a route linking the arithmetic processing unit 75 to the changeover unit 76 is ensured, while when the second contact is selected, a route linking the arithmetic processing unit 75 to the built-in resistance 79 is ensured.

A resistance value of the built-in resistance 79 connected to the second contact of the changeover unit 762 is, for example, 50Ω.

According to the catheter system of this embodiment, a test mode is selected, whereby whether the power source device 701 is normally actuated or not can be confirmed.

Specifically, when the test mode switch 745 is inputted, the contact of the changeover unit 762 is changed over to the second contact by the arithmetic processing unit 75 to ensure a route from the arithmetic processing unit 75 to the built-in resistance 79 via the changeover unit 762, whereby the resistance value of the built-in resistance 79 can be measured. Since the resistance value measured is displayed on the display means 78, whether the resistance value displayed corresponds to the already known resistance value (50Ω) or not (whether the resistance between the electrode groups can be exactly measured or not when the defibrillation catheter is connected) can be confirmed.

In addition, the energy-applying switch 744 is inputted in the test mode, whereby a direct current voltage can be applied to the built-in resistance 79, and the applied record is displayed on the display means 78. Whether the energy as set can be applied to the built-in resistance 79 (whether the predetermined energy can be applied or not when the defibrillation catheter is connected) can be thereby confirmed.

REFERENCE SIGNS LIST
100 Defibrillation catheter
10 Multi-lumen tube
11 First lumen
12 Second lumen
13 Third lumen
14 Fourth lumen
15 Fluororesin layer
16 Inner (core) part
17 Outer (shell) part
18 Stainless steel wire
20 Handle
21 Handle body
22 Lug
24 Strain relief
26 First insulated tube
27 Second insulated tube
28 Third insulated tube
31G First DC electrode group
31 Ring-like electrodes
32G Second DC electrode group
32 Ring-like electrodes
33G Proximal-side potential-measuring electrode group
33 Ring-like electrodes
35 Distal-end tip
41G First lead wire group
41 Lead wires
42G Second lead wire group
42 Lead wires
43G Third lead wire group
43 Lead wires
50 Connector of defibrillation catheter
51, 52, 53 Pin terminals
55 Partition plate
58 Resin
61 First protecting tube
62 Second protecting tube
65 Pull wire
700 Power source device
71 DC power source unit
72 Catheter-connected connector
721, 722, 723 Terminals
73 Electrocardiograph-connected connector
74 External switch (input means)
741 Mode changing-over switch
742 Application energy setting switch
743 Charging switch
744 Energy-applying switch (discharging switch)
745 Test mode switch
75 Arithmetic processing unit
751 Output circuit
76 Changeover unit
762 Changeover unit
77 Electrocardiogram input connector
78 Display means
79 Built-in resistance
800 Electrocardiograph
900 Cardiac potential-measuring means

The invention claimed is:

1. An intracardiac defibrillation catheter system comprising a defibrillation catheter having electrodes and being operable to be inserted into a cardiac cavity for carrying out defibrillation, a power source device for applying a direct current voltage to the electrodes of the defibrillation catheter, and an electrocardiograph, wherein the defibrillation catheter comprises:
    an insulated tube member,
    a first electrode group comprising a plurality of said electrodes, which are ring-like, and which are installed in a distal region of the tube member,
    a second electrode group comprising a plurality of said electrodes, which are ring-like, and which are installed on the tube member towards proximal direction from the first electrode group,
    a first lead wire group comprising a plurality of lead wires whose distal ends are connected to the respective electrodes making up the first electrode group, and
    a second lead wire group comprising a plurality of lead wires whose distal ends are connected to the respective electrodes making up the second electrode group,
    wherein the power source device comprises:
    a DC power source unit,
    a catheter-connected connector which is a connector for the power source device, and is connected to proximal sides of the first lead wire group and the second lead wire group of the defibrillation catheter,
    an electrocardiograph-connected connector which is connected to an input terminal of the electrocardiograph,
    an external switch which is an input means;
    an arithmetic processing unit which controls the DC power source unit based on input of the external switch, the arithmetic processing unit has an output circuit for outputting a direct current voltage from the DC power source unit, and
    a changeover unit comprising a changeover switch of two contacts per circuit which includes a common contact, a first contact and a second contact, in which the catheter-connected connector is connected to the common contact of the changeover unit, the electrocardiograph-connected connector is connected to the first contact of the changeover unit, and the arithmetic processing unit is connected to the second contact of the changeover unit, wherein when a cardiac potential is measured by said electrodes of the defibrillation catheter, the common contact of the changeover unit is connected to the first contact in the changeover unit by the arithmetic processing unit based on input of the external switch, and cardiac potential information from the defibrillation catheter is inputted into the electrocardiograph via the catheter-connected connector, the changeover unit and the electrocardiograph-connected connector of the power source device, and during defibrillation, the common contact of the changeover unit is changed over to the second contact of the changeover unit by the arithmetic processing unit of the power source device such that voltages different in polarity from each other are applied to the first electrode group and the second electrode group of the defibrillation catheter, and each polarity is reversed in sign over time, via the output circuit of the arithmetic processing unit, the changeover unit and the catheter-connected connector from the DC power source unit.

2. The intracardiac defibrillation catheter system according to claim 1, wherein the defibrillation catheter further comprising:

a potential-measuring electrode group comprising a plurality of said electrodes, which is installed on the insulated tube member apart from the first electrode group and the second electrode group, and a lead wire group for potential measurement, comprising a plurality of lead wires whose distal ends are connected to the respective electrodes making up the potential-measuring electrode group, and whose proximal ends are connected to the catheter-connected connector of the power source device, and a conductive path directly linking the catheter-connected connector to the electrocardiograph-connected connector is formed in the power source device, wherein each of the electrodes making up the potential-measuring electrode group is electrically connected to an input terminal of the electrocardiograph via each of the lead wires making up the lead wire group for potential measuring, the catheter-connected connector of the power source device, the conductive path, and the electrocardiograph-connected connector.

3. The intracardiac defibrillation catheter system according to claim 1 or 2, further comprising a cardiac potential-measuring means which is connected to the electrocardiograph.

4. The intracardiac defibrillation catheter system according to claim 3, wherein the cardiac potential-measuring means is an electrode pad or an electrode catheter.

5. The intracardiac defibrillation catheter system according to claim 1, wherein the power source device comprises an electrocardiogram input connector connected to the arithmetic processing unit and an output terminal of the electrocardiograph, and a display means connected to the arithmetic processing unit, and cardiac potential information inputted into the electrocardiogram input connector from the electrocardiograph is inputted into the arithmetic processing unit and displayed on the display means.

6. The intracardiac defibrillation catheter system according to claim 5, wherein the arithmetic processing unit of the power source device conducts arithmetic processing so as to apply a voltage synchronizing with a cardiac potential waveform inputted via the electro-cardiogram input connector to control the DC power source unit.

7. The intracardiac defibrillation catheter system according to claim 1, wherein the arithmetic processing unit of the power source device measures a resistance between the first electrode group and the second electrode group of the intracardiac defibrillation catheter prior to the application of the voltage to judge whether the resistance measured exceeds a fixed value or not, and sends the DC power source unit a control signal to the effect that the voltage is applied only when the resistance does not exceed the fixed value.

* * * * *